US005849526A

United States Patent [19]
Pichersky

[11] Patent Number: 5,849,526
[45] Date of Patent: Dec. 15, 1998

[54] USE OF LINALOOL SYNTHASE IN GENETIC ENGINEERING OF SCENT PRODUCTION

[75] Inventor: Eran Pichersky, Chelsea, Mich.

[73] Assignee: The Regents of the University of Michigan, Ann Arbor, Mich.

[21] Appl. No.: 732,192

[22] Filed: Oct. 15, 1996

[51] Int. Cl.$^6$ .......................... C12P 21/00; C07H 21/04; C12N 5/00; C12N 15/63

[52] U.S. Cl. ...................... 435/69.1; 435/243; 435/320.1; 435/325; 435/410; 536/23.6; 800/205

[58] Field of Search .................................. 435/69.1, 243, 435/320.1, 325, 410; 536/23.6; 800/205

[56] References Cited

PUBLICATIONS

Alonso et al., "Purification of 4S–Limonene Synthase, a Monoterpene Cyclase from the Glandular Trichomes of Peppermint (Mentha x piperita) and Spearmint (*Mentha spicata*)," *J. Biological Chemistry*, 267(11):7582–7587, 1992.

An et al., "Transofrmation of Tobacco, Tomato, Potato, and *Arabidopsis thaliana* Using a Binary Ti Vector System," *Plant Physiol*, 81:301–305, 1986.

Baskin et al., "Improvements in Immunostaining Samples Embedded in Methacrylate: Localization of Microtubules and Other Antigens Throughout Developing Organs in Plants of Diverse Taxa," *Planta*, 187:405–413, 1992.

Bevan et al., "Structure and Transcription of the Nopaline Synthase Gene Region of T–DNA," *Nucleic Acids Research*, 11(2):1983.

Blum et al., "Improved Silver Staining of Plant Proteins, RNA and DNA in Plyacrylamide Gels," *Electrophoresis*, 8:93–99, 1987.

Bouchez et al., "The ocs–Element is a Component of the Promoters of Several T–DNA and Plant Viral Genes," *The EMBO J*, 8(13):4197–4204, 1989.

Bradford, "A Rapid and Sensitive Method for the Quantittion of Microgram Quantities of Protein Utilizing the Principle of Protein–Dye Binding," *Analytical Biochemistry*, 72:248–254, 1976.

Callis et al., "Introns Increase Gene Expression in Cultured Maize Cells," *Genes & Development*, 1:1183–1200, 1987.

Chandler et al., "Two Regulatory Genes of the Maize Anthocyanin Pathway are Homologous: Isolation of B Utilizing R Genomic Sequences," *The Plant Cell*, 1:1175–1183, Dec. 1989.

Christou et al., "Stable Transformation of Soybean Callus by DNA–Coated Gold," *Plant Physiol*, 87:671–674, 1988.

Conkling et al., "Isolation of Transcriptionally Regulated Root–Specific Genes from Tobacco," *Plant Physiol*, 93:1203–1211, 1990.

Cox and Goldberg, "Analsis of Plant Gene Expression," *In: Plant Molecular Biology, A Practical Approach*, Shaw (Ed.), Chapter 1:1–35, 1988.

Croteau and Cane, "Monoterpene and Sesquiterpene Cyclases," *Methods in Enzym*, 110:383–405, 1985.

Croteau and Satterwhite, "Method for Radio–Capillary Gas Chromatography Employing a Modified Oxidation–Reduction Train and Flow–Through Detector," *J Chromatography*, 500:349–354, 1990.

Croteau et al., "Biosynthesis of Monoterpenes: Partial Purification, Characterization, and Mechanism, of Action of 1,8–Cineole Synthase," *Arch Biochem Biophysics*, 309(1):184–192, Feb. 1994.

Croteau, "Biochemistry of Monoterpenes and Sesquiterpenes of the Essential Oils," *In: Herbs, Spices, and Medicinal Plants: Recent Advances in Botany, Horticulture, and Pharmacology*, 1:81–133, 1986.

Croteau, "Biosynthesis and Catabolism of Monoterpenoids," *Chem Rev*, 87:929–954, 1987.

Dobson et al., "Differences in Fragrance Chemistry Between Flower Parts of *Rosa Rugosa* Thunb. (Rosaceae)," *Israel J of Botany*, 39:143–156, 1990.

Dodson et al., "Biologically Active Compounds in Orchid Fragrances," *Science*, 164:1243–1249, Jun. 1969.

Dudareva et al., "Evoluation of Floral Scent in Clarkia: Novel Patterns of S–Linalool Synthase Gene Expression in the C. Breweri Flower," *The Plant Cell*, 8:1137–1148, Jul. 1996.

Ebert et al., "Identification of an Essential Upstream Element in the Nopaline Synthase Promoter by Stableand transient Assays," *Proc. Natl Acad Sci, USA*, 84:745–5749, Aug. 1987.

Ellis et al., "The ocs Element: a 16 Base Pair Palindrome Essential for Activity of the Octopine Synthase Enhancer," *The EMBO J*, 6(11):3203–3208, 1987.

Forde, "4 AT–Rich Elements (ATREs) in the Promoter Regions of Nodulin and Other Higher Plant Genes: A Novel Class of Cis–Acting Regulatory Element?" *Results and Problems in Cell Differentiation*, 20:87–103, 1994.

Fromm et al., "An Octopine Synthase Enhancer Element Directs Tissue–Specific Expression and Binds ASF–1, A Factor from Tobacco Nuclear Extracts," *The Plant Cell*, 1:977–984, Oct. 1989.

Galen and Kevan, "Bumblebee Foraging and Floral Scent Dimorphism: *Bombus Kirbyellus* Curtis (Hymeoptera: Apidae) and *Polemonium viscosum* Nutt. (Polemoniaceae)," *Can J Zool*, 61:1207–1213, 1983.

Galen, "Regulation of Seed–Set in *Polemonium Viscosum*: Floral Scents, Pollination, and Resources," *Ecology*, 66(3):792–797, 1985.

(List continued on next page.)

Primary Examiner—George C. Elliott
Assistant Examiner—Robert Schwartzman
Attorney, Agent, or Firm—Arnold, White & Durkee

[57] ABSTRACT

A purified S-linalool synthase polypeptide from *Clarkia breweri* is disclosed as is the recombinant polypeptide and nucleic acid sequences encoding the polypeptide. Also disclosed are antibodies immunoreactive with the purified peptide and with recombinant versions of the polypeptide. Methods of using the nucleic acid sequences, as well as methods of enhancing the smell and the flavor of plants expressing the nucleic acid sequences are also disclosed.

32 Claims, 4 Drawing Sheets

OTHER PUBLICATIONS

Gallie et al., "Visualizing mRNA Expression in Plant Protoplasts: Factors Influencing Efficient mRNA Uptake and Translation," *The Plant Cell,* 1:301–311, Mar. 1989.

Gambliel and Croteau, "Biosynthesis of (±)-α-Pinene and (-)-β-Pinene from Geranyl Pyrophosphate by a Soluble Enzyme System from Sage (*Salvia officinalis*)," *J Biological Chemistry,* 257(5):2335–2342, Mar. 1982.

Gambliel and Croteau, "Pinene Cyclases I and II," *J Biological Chemistry,* 259(2):740748, Jan. 1984.

Gijzen et al., "Conifer Monoterpenes, Biochemistry and Bark Beetle Chemical Ecology," *In: Bioactive Volatile Compounds from Plants,* Teranishi et al. (Eds.), ACS Symposium Series 525, Washington, DC, Chapter 2:8–22, 1992.

Giuliano et al., "A Light–Entrained Circaidian Clock controls Transcription of Several Plant Genes," *The EMBO J,* 7(12):3635–3642, 1988.

Harborne, "Recent Advances in the Ecological Chemistry of Plant Terpenoids," *In: Ecological Chemistry and Biochemistry of Plant Terpenoids,* Harborne and Barberan (Ed.), London: Clarendon Press, Chapter 16:399–426, 1991.

Hemleben and Zentgraf, "Structural Organization and Regulation of Transciption by RNA Polymerase I of Plant Nuclear Ribosomal RNA Genes," *In: Results and Problems in Cell Differentiation,* 20:3–24, 1994.

Hudspeth and Grula, "Structure and Expression of the Maize Gene Encoding the Phophoenolpyruvate Carboxylase Isozyme Involved in $C_4$ Phostosynthesis," *Plant Molecular Biology,* 12:579–589, 1989.

Kellmann et al., "Concerted Circadian Oscillations in Transcript Levels of Nentenn *Lha/b* (*cab*) *Genes in Lycopersicon Esculentum* (Tomato)," *Mol Gen Genet,* 237:439–448, (1993).

Knudsen and Tollsten, "Trends in Floral Scent Chemistry in Pollination Syndromes: Floral Scent Composition in Moth--Pollinated Taxa," *Botanical J of the Linnean Society,* 113:263–284, 1993.

Knudsen et al., "Floral Scents–A Checklist of Volatile Compounds Isolated by Head–Space Techniques," *Phytochemistry,* 33(2):253–280, 1990.

Kyte and Doolittle, "A Simple Method for Displaying the Hydropathic Character of a Protein," *J Mol Biol,* 157:105–132, 1982.

Laemmli, "Cleavage of Structural Proteins During the Assembly fo the Head of Bacteriophage T4," *Nature,* 227:680–685, Aug. 1970.

Langenheim, "Higher Plant Terpenoids: a Phytocentric Overview of Their Ecological Roles," *J Chemical Ecology,* 20(6):1223–1280, 1994.

Lawton et al., "Expression of a Soybean β–Conclycinin Gene Under the Control of the Cauliflower Mosaic Virus 35S and 19S Promoters in Transformed Petunia Tissues," *Plant Molecular Biology,* 9:315–324, 1987.

Lewinsohn et al., "Defense Mechanisms of Conifers," *Plant Physiol,* 96:38–43, 1991.

Lewinsohn et al., "Regulation of Monoterpene Biosynthesis in Conifer Defense," *In: Regulation of Isopentenoid Metabolism,* Nes et al. (Eds.), ACS Symposium Series 497, Washington, DC, Chapter 2:8–17, 1992.

Lewinsohn et al., "Wound–Inducible Pinene Cyclase from Grand Fir: Purification, Characterization, and renaturation after SDS–Page," *Arch Biochem and Biophysics,* 293(1):167–173, Feb. 1992.

Loughrin et al., "Circadian Rhythm of Volatile Emission from Flowers of *Nicotiana Sylvestris* and *N. Suaveolens,*" *Physiologia Plantarum,* 83:492–496, 1991.

Loughrin et al., "Glycosidically Bound Volatile Compounds of *Nicotiana Sylvestris* and *N. Suaveolens* Flowers," *Phytochemistry,* 31(5):1537–1540, 1992.

Loughrin et al., "Volatiles from Flowers of *Nicotiana Sylvestris, N. Otophora* and *Malus x Domestica*: Headspace Components and Day–Night Changes in Their Relative Concentrations," *Phytochemistry,* 29(8):2473–2477, 1990.

MacSwain et al., "Comparative Behavior of Bees and Onagraceae. IV. Clarka Bees of the Western United States," *University of California Publications Enotomology,* Belkin et al. (Eds.), London:University of California Press, Ltd., 70:1–80, 1973.

Matile and Altenburger, "Rhythms of Fragrance Emission in Flowers," *Planta,* 174:242–247, 1988.

McGraht et al., "Duplicate Sequences with a Similarity to Expressed Genes in the Genome of *Arabidopsis Thaliana,*" *Theor Appl Genet,* 86:880–888, 1993.

Nagai and Thøgersen, "Synthesis and Sequence–Specific Proteolysis of Hybrid Proteins Produced in *Escherichia Coli,*" *Methods in Enzymology,* 153:461–481, 1987.

Odell et al., "Identification of DNA Sequences Required for Activity of the Cauliflower Mosaic Virus 35S Promoter," *Nature,* 313:810–812, Feb. 1985.

Omirulleh et al., "Activity of a Chimeric Promoter with the Doubled CaMV 35S Enhancer Element in Protoplast–Derived Cells and Transgenic Plants in Maize," *Plant Molecular Biology,* 21:415–428, 1993.

Overland, "Endogenous Rhythm in Opening and Odor in Flowers of Cestrum Nocturnum," *Am J Bot,* 47:378–382, May 1960.

Pellmyr, "Three Pollination Morphs in *Cimicifuga Simplex*; Incipient Speciation Due to Inferiority in Competition," *Oecologia,* 68:304–307, 1986.

Pichersky et al., "A New Member of the CAB Gene Family: Structure, Expression and Chromosomal Lopcation of Cab–8, the Tomato Gene Encoding the Type III Chlorophyll a/b–binding Polypeptide of Photosystem I," *Plant Mol Biology,* 12:257–270, 1989.

Pichersky et al., "Floral Scent Production in Clarkia (Onagraceae). I. Localization and Developmental Modulation of Monoterpene Emission and Linalool Synthase Activity," *Plant Physiol.,* 106:1533–1540, 1994.

Pichersky et al., "Fragments of Plastid DNA in the Nuclear Genome of Tomato: Prevalence, Chromosomal Location, and Possible Mechanism of Integration," *Mol Gen Genet,* 225:453–458, 1991.

Pichersky et al., "Molecular Characterization and Genetic Mapping of DNA Sequences Encoding the Type I Chlorophyll a/b–binding Polypeptide of Photosystem I in *Lycopersicon Esculentum* (Tomato)" *Plant Molecular Biology,* 9:205–216, 1987.

Pichersky et al., "Nucleotide Sequence and Chromosomal Location of Cab–7, the Tomato Gene Encoding the Type II Chlorophyll a/b–binding Polypeptide of Photosystem I," *Plant Molecular Biology,* 11:69–71, 1988.

Pichersky et al., "Purification and Characterization of S–Linalool Synthase, an denzyme Involved in the Production of Floral Scent in *Clarkia Breweri,*" *Arch Biochem and Biophysics,* 316(2):803–807, Feb. 1995.

Pichersky et al., "The Tomato Cab–4 and Cab–5 Genes Encode a Second type of CAB Polypeptides Localized in Photosystem II," *Plant Molecular Biology,* 9:109–120, 1987.

Piechulla et al., "Determination of Steady–State mRNA Levels of Individual Chlorohyll a/b Binding Protein Genes of the Tomato Cab Gene Family," *Mol Gen Genet,* 230–413–422, 1991.

Raguso and Pickersky, "Floral Volatiles from *Clarkia Breweri* and *C. Concinna* (*Onagraceae*): Recent Evolution of Floral Scent and Moth Pollination," *Pl syst Evol,* 194:55–67, 1995.

Rajaonarivony et al., "Characterization and Mechanism of (4S)–Limonene Synthase, A Monoterpene Cyclase from the Glandular Trichomes of Peppermint (*Mentha X Piperita*)," *Arch of Biochem and Biophysics,* 296(1):49–57, Jul. 1992.

Stern et al., "Osmophores of Stanhopea (Orchidaceae)," *Amer J Bot,* 74(9):1323–1331, 1987.

Studier et al., "Use of T7 RNA Polymerase to Direct Expression of Cloned Genes," *Methods in Enzymology,* 185:60–89, 1990.

Sullivan et al., "Isolation and Characterization of a Maize Chlorophyll a/b Binding Protein Gene That Produces High Levels of mRNA in the Dark," *Mol Gen Genet,* 215:431–440, 1989.

Tabor and Richardson, "A Bacteriophage T7 RNA Polymerase/Promoter System for Controlled Exclusive Expression of Specific Genes," *Proc Natl Acad Sci, USA,* 82:1074–1078, Feb. 1985.

Turlings and Tumlinson, "Systemic Release of Chemical Signals by Herbivore–Injured Corn," *Proc Natl Acad Sci, USA,* 89:8399–8402, Sep. 1992.

Turlings et al., "Exploitation of Hervivore–Induced Plant Odors by Host–Seeking Parasitic Wasps," *Science,* 250:1251–1253, Nov. 1990.

Vasil et al., "Increased Gene Expression by the First Intron of Maize Shrunken–I Locus in Grass Species," *Plant Physiol,* 91:1575–1579, 1989.

Walker et al., "DNA Sequences Required for Anaerobic Expression of the Maize Alcohol Dehydrogenase 1 Gene," *Proc Natl Acad Sci, USA,* 84:6624–6628, Oct. 1987.

Wang et al., "Characterization of cis–Acting Elements Regulating Transcription from the Promoter of a Constitutively Active Rice Actin Gene," *Molecular and Cellular Biology,* 12(8):3399–3046, Aug. 1992.

Watanabe et al., "Formation of Flower Fragrance Compounds from Their Precursors by Enzymic Action During Flower Opening," *Biosci Biotech Biochem,* 57(7):1101–1106, 1993.

Wheeler and Croteau, "Terpene Cyclase Catalysis in Organic Solvent/Minimal Water Media: Demonstration and Optimization of (+)–α–Pinene Cyclase Activity," *Arch of Biochemistry and Biophysics,* 248(1):429–434, Jul. 1986.

Wilmink et al, "Activity of Constitutive Promoters in Various Species from the Liliaceae," *Plant Molecular Biology,* 28:949–955, 1995.

Winterhalter et al., "6,7–Epoxy–Linalool and Related Oxygenated terpenoids from *Carica Papaya* Fruit," *Phytochemistry,* 25(6):1347–1350, 1986.

Yang and Russell, "Maize sucrose Synthase–1 Promoter Directs Phloem Cell–Specific Expression of Gus Gene in Transgenic Tobacco Plants," *Proc Natl Acad Sci, USA,* 87:4144–4148, Jun. 1990.

5,849,526

1

USE OF LINALOOL SYNTHASE IN GENETIC ENGINEERING OF SCENT PRODUCTION

The government owns rights in the present invention pursuant to grant number MCB 9218989 and IBN 9417582 from the National Science Foundation. The government may also own rights in the present invention pursuant to grant number GM 31354 by the National Institutes of Health and grant number DE-FG06-88ER-13869 from the Department of Energy.

BACKGROUND OF THE INVENTION

1. Field of the Invention

The present invention relates generally to the fields of the floral emission of monoterpenes and the production of monoterpenes by plants. The present invention also relates to the field of the production of enhanced scent and taste in plants.

2. Description of the Related Art

Flowers of many plants attract pollinators by producing and emitting volatile compounds. The scent emitted by such flowers is often a complex mixture of low molecular weight compounds, and the relative abundances and interactions of the constituents give the flower its particular characteristic fragrance. Floral scents have been demonstrated to function as long and short-distance attractants and nectar guides to a variety of animal pollinators (reviewed in Dobson, 1993). Moreover, insects are able to distinguish between complex floral scent mixtures (Dodson et al., 1969; Pellmyr, 1986). Discriminatory visitation based on floral scent has important implications for population structure and reproductive isolation in both temperate (Galen and Kevan, 1983; Galen, 1985; Pellmyr, 1986) and tropical plant species (Dodson et al., 1969). Thus, floral scent is of paramount importance to plant reproduction and evolution.

Several thousand compounds have been identified from various floral scents, mostly by steam distillation or headspace trapping in combination with gas chromatography-mass spectrometry (GC-MS) (Knudsen et al., 1993). Most of these compounds are either terpenoids, benzenoid compounds, or acyl lipid derivatives (Croteau and Karp, 1991). Although perfumers still survey natural sources for novel fragrance compounds (Joulain, 1987; Kaiser, 1991), this information is most often used in directing organic syntheses to imitate natural fragrances or create new combinations. There is a need, therefore, for purified synthetic enzymes that can be produced in commercial quantities for use in the manufacture of fragrance.

*Clarkia breweri* (Onagraceae), an annual plant native to California, has a strong, sweet fragrance, consisting of some 8–12 different volatiles that fall into two groups: monoterpenoids and benzenoids (Raguso and Pichersky, 1995). A major component of the scent is linalool, an acyclic monoterpene common to the floral scents of numerous other plant species (Kaiser, 1991; Knudsen et al., 1993). Two cyclic isomers of linalool oxide are also produced by *C. breweri* (FIG. 1), almost certainly by further oxidative modification of linalool.

Monoterpenes are a large and diverse group of natural products. Due to their volatility, and thus their ability to be perceived at a distance, they are often involved in plant-insect interactions (Harborne, 1991; Langenheim, 1994). In addition to pollinator attraction (Dobson et al., 1993; Knudsen et al., 1993b), monoterpenes also play an important role in plant defense (Langenheim, 1994; Lewinsohn et al.,

2

1992a) or may act as semio-chemicals (Turlings et al., 1990; Gijzen, 1993). Monoterpenes are also of commercial value as essential oils for perfumery and flavoring use and as industrial raw materials (Dawson, 1994). Monoterpenes are derived from the ubiquitous isoprenoid intermediate GPP by a class of enzymes called monoterpene synthases (also termed cyclases when they catalyze the formation of cyclic products). Although many monoterpene synthases from plants have been described, only a few of these enzymes have been purified to homogeneity and characterized in detail (Alonso et al., 1992; Lewinsohn et al., 1992b). In addition, few if any of the genes encoding these enzymes have been identified.

There is an immediate need, therefore, for the identification and isolation of genes encoding the monoterpene synthases for use in the manufacturing of important chemicals for the fragrance and agronomic industries, and for the engineering of commercially important plants with enhanced characteristics.

SUMMARY OF THE INVENTION

The present invention seeks to overcome these and other drawbacks inherent in the prior art by providing a purified linalool synthase polypeptide and by further providing an isolated nucleic acid segment encoding the linalool synthase polypeptide.

As such, an important embodiment of the invention may be described as an isolated nucleic acid segment comprising a nucleic acid sequence encoding a linalool synthase protein or polypeptide. In particular, the nucleic acid sequence may encode an S-linalool synthase polypeptide and may more particularly encode a *Clarkia breweri* S-linalool synthase polypeptide. In even more particular embodiments, the isolated nucleic acid segment of the present invention may encode the amino acid sequence disclosed herein as SEQ ID NO:2.

In certain embodiments, the invention may also be described as a nucleic acid segment comprising a nucleic acid sequence consisting essentially of the nucleic acid sequence of SEQ ID NO:1. It is evident, due to the degeneracy of the genetic code and the functional equivalency of certain amino acids within a polypeptide sequence, that nucleic acid sequences may vary considerably, and still encode essentially the same polypeptide. Therefore, a nucleic acid sequence may be altered for various reasons that include, but are not limited to the use of codons that occur more frequently in the gene sequences of a particular host organism, or to insert or delete a restriction enzyme recognition site for ease in moving the particular sequence into or out of a vector, without altering the function of the polypeptide. So, while it is understood that an embodiment of the present invention is a nucleic acid segment that has the nucleic acid sequence of SEQ ID NO:1, certain variations as described are also encompassed by the present invention.

It will also be understood that amino acid and nucleic acid sequences may include additional residues, such as additional N- or C-terminal amino acids, and yet still be essentially as set forth in one of the sequences disclosed herein, so long as the sequence meets the criteria set forth above. This particularly applies to nucleic acid sequences which may, for example, include various non-coding sequences flanking either of the 5' or 3' portions of the coding region or may include various internal sequences, i.e., introns, which are known to occur within genes.

As used herein, the term "nucleic acid segment" is intended to refer to a nucleic acid molecule which has been isolated free of total cellular DNA or RNA, as the case may be, of a particular species. Therefore, a nucleic acid segment encoding a linalool synthase is intended to refer to a nucleic acid segment which contains such coding sequences yet is isolated away from total RNA or DNA of a *Clarkia breweri* cell. Included within the term "nucleic acid segment", are DNA segments, whether isolated from genomic or cDNA sources or even prepared synthetically, and RNA segments which may be isolated MRNA or RNA obtained by in vitro or in vivo transcription of a DNA segment, or a chemically synthesized RNA molecule. The term also includes DNA or RNA segments which may be employed in the preparation of vectors, as well as the vectors themselves, including, for example, plasmids, cosmids, phage, viruses, and the like. For example, various types of DNA composition may be used for delivery to recipient cells in accordance with the present invention. For example, DNA segments in the form of vectors and plasmids, or linear DNA fragments, in some instances containing only the DNA element to be expressed in the plant, and the like, may be employed. Vectors, plasmids, cosmids, YACs (yeast artificial chromosomes) and DNA segments for use in transforming such cells will, of course, generally comprise the Lis gene. These DNA constructs can further include structures such as promoters, enhancers, polylinkers, or even regulatory genes as desired.

In certain embodiments, the nucleic acid segments of the present invention may be positioned under the control of a promoter, and may even be positioned under the control of a recombinant promoter. For example, the promoter may be in the form of the promoter which is naturally associated with a linalool synthase gene in *Clarkia breweri* cells, as may be obtained by isolating the 5' non-coding sequences located upstream of the coding segment or exon. In other embodiments, it is contemplated that certain advantages will be gained by positioning the coding nucleic acid segment under the control of a recombinant, or heterologous, promoter. As used herein, a recombinant or heterologous promoter is intended to refer to a promoter that is not normally associated with a linalool synthase gene in its natural environment. Preferred constructs will generally include a plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang & Russell, 1990), α-tubulin, actin (Wang et al., 1992), cab (Sullivan et al., 1989), PEPCase (Hudspeth & Grula, 1989) or those associated with the R gene complex (Chandler et al., 1989). Other plant promoters are well known in the art as evidenced by the literature (Forde, 1994; Hemleben and Zentgraf, 1994; Wilmink et al., 1995, each incorporated herein by reference) and would function in the practice of the present invention Tissue specific promoters such as root cell promoters (Conkling et al., 1990) and tissue specific enhancers (Fromm et al., 1989) are also contemplated to be particularly useful, as are inducible promoters such as ABA- and turgor-inducible promoters. Naturally, it will be important to employ a promoter that effectively directs the expression of the nucleic acid segment in the cell type chosen for expression. The use of promoter and cell type combinations for protein expression is generally known to those of skill in the art of molecular biology, (for example, see Sambrook et al. (1989); Methods in Plant Molecular Biology and Biotechnology, Eds: B. R. Glick, J. E. Thompson. CRC Press, 1993; Gelvin et al., 1990). The promoters employed may be constitutive, or inducible, and can be used under the appropriate conditions to direct high level expression of the introduced nucleic acid segment, such as is advantageous in the large-scale production of recombinant proteins or peptides. Appropriate promoter systems contemplated for use in high-level expression include, but are not limited to, the T7 RNA polymerase promoter system described by Tabor & Richardson (1985) and the maltose binding protein-fusion protein system (Nagai & Thogersen, 1987).

Constructs will also include the Lis gene along with a 3' end DNA sequence that acts as a signal to terminate transcription and allow for the poly-adenylation of the resultant mRNA. The most preferred 3' elements are contemplated to be those from the nopaline synthase gene of Agrobacterium tumefasciens (Bevan et al., 1983), the terminator for the T7 transcript from the octopine synthase gene of Agrobacterium tumefasciens, and the 3' end of the protease inhibitor I or II genes from potato or tomato. Regulatory elements such as Adh intron 1 (Callis et al., 1987), sucrose synthase intron (Vasil et al., 1989) or TMV omega element (Gallie, et al., 1989), may further be included where desired.

As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e., to include a preferred consensus leader sequence which may increase or maintain MRNA stability and prevent inappropriate initiation of translation. The choice of such sequences will be known to those of skill in the art in light of the present disclosure. Sequences that are derived from genes that are highly expressed in plants, and in floral or fruit tissue in particular, will be most preferred.

It is contemplated that vectors for use in accordance with the present invention may be constructed to include the ocs enhancer element. This element was first identified as a 16 bp palindromic enhancer from the octopine synthase (ocs) gene of agrobacteriurn (Ellis et al., 1987), and is present in at least 10 other promoters (Bouchez et al., 1989). It is proposed that the use of an enhancer element, such as the ocs element and particularly multiple copies of the element, will act to increase the level of transcription from adjacent promoters when applied in the context of transformation.

Alternatively, one may wish to obtain novel tissue-specific promoter sequences for use in accordance with the present invention. To achieve this, one may first isolate cDNA clones from the tissue concerned and identify those clones which are expressed specifically in that tissue, for example, using Northern blotting. Ideally, one would like to identify a gene that is not present in a high copy number, but which gene product is relatively abundant in specific tissues. The promoter and control elements of corresponding genomic clones may then be localized using the techniques of molecular biology known to those of skill in the art.

The production of a transformed cell includes the introduction of an exogenous DNA segment, such as a cDNA or gene, into a recipient cell to create the transformed cell. The frequency of occurrence of cells receiving DNA is believed to be low. Moreover, it is most likely that not all recipient cells receiving DNA segments will result in a transformed cell wherein the DNA is stably integrated into the plant genome and/or expressed. Some may show only initial and transient gene expression. However, certain cells from virtually any plant species may be stably transformed, and these cells developed into transgenic plants, through the application of the techniques known in the art.

There are many methods for introducing transforming DNA segments into cells, but not all are suitable for delivering DNA to plant cells. Suitable methods are believed to include virtually any method by which DNA can be introduced into a plant cell, such as by Agrobacterium infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Where one wishes to introduce DNA by means of electroporation, certain cell wall-degrading enzymes, such as pectin-degrading enzymes, may be employed to render the target recipient cells more susceptible to transformation by electroporation than untreated cells. Alternatively, recipient cells are made more susceptible to transformation, by mechanical wounding.

To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding the cell in a controlled manner. Such cells would then be recipient to DNA transfer by electroporation, which may be carried out at this stage, and transformed cells then identified by a suitable selection or screening protocol dependent on the nature of the newly incorporated DNA.

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducibly stably transforming plant cells, is that neither the isolation of protoplasts (Cristou et al., 1988) nor the susceptibility to Agrobacterium infection is required. An illustrative embodiment of a method for delivering DNA into cells by acceleration is a Biolistics Particle Delivery System, which can be used to propel particles coated with DNA or cells through a screen, such as a stainless steel or Nytex screen, onto a filter surface covered with cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation.

The nucleic acid segments of the present invention may also be defined as recombinant vectors when the nucleic acid sequences disclosed and described herein are combined with, or joined to nucleic acid sequences that allow the transformation of those sequences into a host cell, and in some cases, replication of those sequences in the host cell. In certain preferred embodiments, the nucleic acid segments may be defined as a recombinant expression vector capable of expressing a linalool synthase protein or polypeptide on introduction into a host cell, or alternatively as a plant transformed with such a recombinant expression vector. In particularly preferred embodiments, the vector comprises a nucleic acid sequence in accordance with SEQ ID NO:1, and the vector may further comprise the pBLUESCRIPT or pBIN19 nucleic acid sequence.

The present invention may, in certain embodiments be defined as a recombinant host cell comprising a nucleic acid segment that encodes a linalool synthase polypeptide. The recombinant host cell may be a prokaryotic cell, such as a bacterial cell, or E. coli cell, or the recombinant host cell may be a eukaryotic cell, with a preferred eukaryotic cell being a yeast cell or a plant cell. In addition, the plant cell may be a part of a plant or a substructure of a plant. It is understood that the nucleic acid segment contained in the host cell may be positioned under the control of a promoter and further that the nucleic acid segment may be positioned in a recombinant vector. The recombinant vector may also be a recombinant expression vector wherein the host cell expresses a linalool synthase polypeptide.

In certain embodiments, the invention may be described as a nucleic acid segment hybridizable to a nucleic acid segment comprising the sequence of SEQ ID NO:1 under stringent conditions, or even as consisting essentially of the complement of SEQ ID NO:1. Stringent conditions are defined as relatively low salt and/or high temperature, such as provided by 0.02M–0.15M NaCl or the equivalent at temperatures of 50° C. to 70° C. Such selective conditions tolerate little, if any, mismatch between the probe and the template or target strand, and would be particularly suitable for isolating linalool synthase genes.

As used herein the term "complement" is used to define the strand of nucleic acid which will hybridize to the first nucleic acid sequence to form a double stranded molecule under stringent conditions. Stringent conditions are those that allow hybridization between two nucleic acid sequences with a high degree of homology, but precludes hybridization of random sequences. For example, hybridization at low temperature and/or high ionic strength is termed low stringency and hybridization at high temperature and/or low ionic strength is termed high stringency. The temperature and ionic strength of a desired stringency are understood to be applicable to particular probe lengths, to the length and base content of the sequences and to the presence of formamide in the hybridization mixture.

It is understood in the art that a nucleic acid sequence will hybridize with a complementary nucleic acid sequence under high stringency conditions even though some mismatches may be present. Such closely matched, but not perfectly complementary sequences are also encompassed by the present invention. For example, differences may occur through genetic code degeneracy, or by naturally occurring or man made mutations and such mismatched sequences would still be encompassed by the present claimed invention.

The nucleic acid sequences disclosed herein will also find utility as probes or primers in nucleic acid hybridization embodiments. As such, it is contemplated that oligonucleotides which comprise a sequence of at least 15, 20, 30, 50, 100, 200, 300, 400, 500, 600, 800, 1000, 1500 or even 2000 contiguous nucleotides which corresponds to at least a 15, 20, 30, 50, 100, 200, 300, 400, 500, 600, 800, 1000, 1500 or even 2000 nucleotide contiguous sequence of SEQ ID NO:1 or its complement will be useful as probes or primers. In addition, nucleic acid segments comprising a sequence of at least 2,583 contiguous nucleotides which corresponds to a sequence of at least 2,583 contiguous nucleotides of SEQ ID NO:1 or its complement, such as the 2,583 contiguous nucleotides of SEQ ID NO:1 that encode the mature protein, for example will be useful for various embodiments, as will a segment comprising a sequence of at least 2,610 contiguous nucleotides which corresponds to a sequence of at least 2,610 contiguous nucleotides of SEQ ID NO:1 or its complement, such as the 2,610 nucleotide sequence encoding the entire coding region of SEQ ID NO:1, or even a nucleic acid segment comprising a sequence of at least 2,681 contiguous nucleotides which corresponds to the 2,681 nucleotide sequence of SEQ ID NO:1 or its complement.

It is also understood that the nucleic acid segments may be contained in various vectors and described above, and that as such, a nucleic acid segment of the present invention may be further defined as a nucleic acid fragment derived from SEQ ID NO:1 or its complement comprising up to 10,000, 5,000, 3,000, 1,000, 500, 100 or even 50 basepairs in length.

In certain embodiments, the invention may also be described as a method of using a nucleic acid segment encoding a linalool synthase protein or polypeptide, comprising the steps of preparing a recombinant vector in which said nucleic acid segment is positioned under the control of a promoter; introducing said recombinant vector into a host cell; culturing said host cell under conditions effective to allow expression of the encoded linalool synthase protein or polypeptide; and collecting said expressed linalool synthase protein or polypeptide.

The invention may also be described in certain embodiments as a method of enhancing the scent production of a plant, comprising the steps of obtaining a recombinant vector capable of expressing a nucleic acid segment encoding a linalool synthase polypeptide on introduction into a plant cell; transforming said plant with said vector; and growing said plant under conditions appropriate for expression of said nucleic acid segment. In the practice of this method, the nucleic acid segment may be under the control of a tissue specific promoter/enhancer, and the tissue specific promoter/enhancer may preferably be specific for floral tissue. In particularly preferred embodiments, the plant is a flowering plant, petunia, rose, carnation, etc., for example.

The present invention may also be described, in certain embodiments as a method of enhancing the flavor of a plant, comprising the steps of obtaining a recombinant vector capable of expressing the nucleic acid segment encoding a linalool synthase polypeptide on introduction into a plant cell; transforming said plant with said vector; and growing said plant under conditions appropriate for expression of said nucleic acid segment, and preferably wherein the nucleic acid segment is under the control of a tissue specific promoter/enhancer, and more preferably wherein the promoter/enhancer is specific for fruit or leaf tissue. Examples of preferred plants for the practice of this method include, but are not limited to tomato, grape and tea plants.

An important embodiment of the present invention is a purified linalool synthase polypeptide having a molecular weight of from about 68 to 79 kDa and a specific activity of at least about 20 pkat/mg or even a specific activity of at least about 44.1 pkat/mg, or even more preferably a specific activity of at least about 395 pkat/mg. It is understood that a 1 pkat unit is defined as 1 picomole of product formed/second.

In certain embodiments, a linalool synthase polypeptide composition of the present invention may be obtained by separating proteins from a flower or a flower part of a *Clarkia breweri* plant. In such a method of obtaining a linalool synthase protein composition, one would first obtain a protein extract by mechanical or enzymatic cellular disruption and centrifugation. The further purification of such a desired protein is well known in the art and within the skill of the skilled practitioner. For example, if further purification is desired, one may pass the crude protein extract over a DEAE-cellulose column or an ion-exchange column and collect the fractions with the highest linalool synthase activity. Those fractions may be identified by measuring the absorbance at 280 nm, for example (to determine the presence of polypeptides), and assaying those fractions containing proteins for linalool synthase activity. Those fractions containing the desired activity may again be further purified if so desired, by pooling those fractions and passing them over a hydroxyapatite column, for example, and again collecting fractions as before. The collected fractions may be even further purified if desired, by passing those fractions over a Mono-Q column and collecting the fractions with linalool synthase activity to obtain said polypeptide. The polypeptide obtained by this method may in certain preferred embodiments consist essentially of the amino acid sequence of SEQ ID NO:2.

A certain embodiment of the present invention is also a recombinant polypeptide comprising as a part of its amino acid sequence, a sequence according to the amino acid sequence set forth as SEQ ID NO:2, or even a recombinant polypeptide that has the amino acid sequence of SEQ ID NO:2.

A certain embodiment of the invention is also an antibody immunoreactive with the polypeptides as defined immediately above. In addition, the antibody may be a polyclonal antibody, or is more preferably a monoclonal antibody.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

The following abbreviations are used throughout the present disclosure: GPP, Geranyl Pyrophosphate; LIS, Linalool Synthase; LSC, Liquid Scintillation; DTT, dithiothreitol; GC, Gas chromatography; LPP, Linalyl pyrophosphate; LIS, S-Linalool synthase; Hepes, N-2-hydroxyethylpiperazine-N'-2-ethanesulfonic acid; Tris, tris (hydroxymethyl)-aminomethane.

DETAILED DESCRIPTION OF THE PREFERRED EMBODIMENTS

Although the importance of scent to the reproductive success of many plants has been well documented, little research in the area of cell and molecular biology has been devoted to it. The inventors' study represents the first example of the isolation and molecular characterization of enzymes and genes involved in scent production. Besides the intrinsic interest in elucidating the mechanisms controlling scent production, such knowledge may accrue practical benefits as well. Some agronomically important plants require pollinators that are attracted by floral scents, and discoveries in this field may eventually lead to improving such crops. For example, some scented tropical trees introduced to the temperate zone are poorly pollinated, with the resulting poor yield, because their scent does not "appeal" to the local insects. Understanding how the production of scent components is regulated may allow us in the future to manipulate such traits and enhance the attractiveness of such flowers to local pollinators.

Figure 1:
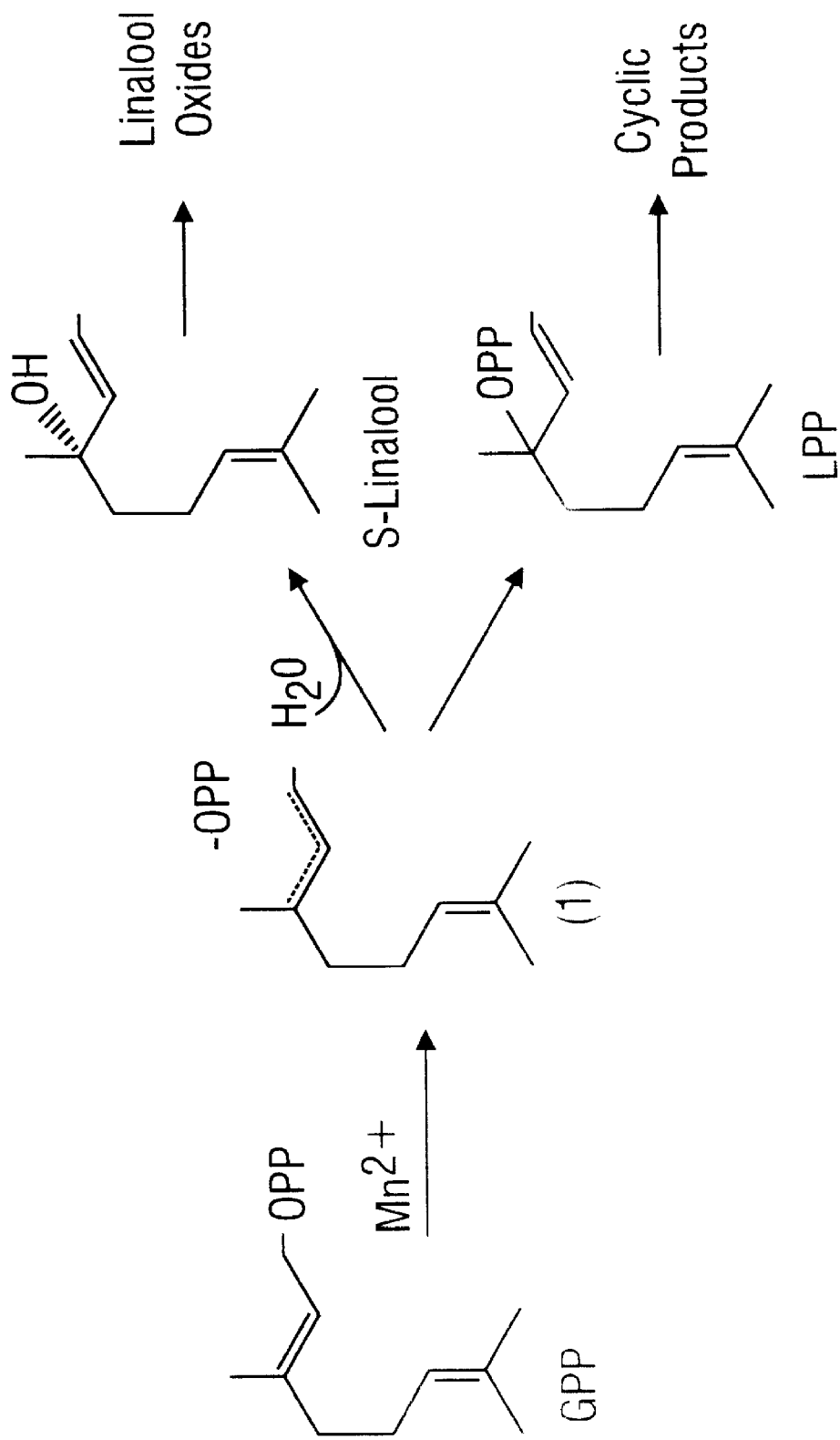
FIG. 1. The formation of S-linalool from GPP by the action of S-linalool synthase and subsequent conversion to S-linalool oxides. S-Linalool synthase and monoterpene cyclases have a similar ionization first step, leading to the intermediate linalyl cation (1). S-linalool is formed by water addition in the reaction catalyzed by S-linalool synthase, whereas the bound LPP (either S- or R-LPP, depending on the particular cyclase) is isomerized and cyclized to cyclohexanoid monoterpenes by monoterpene cyclases.

A major component of the scent of C. breweri flowers is linalool, an acyclic monoterpene alcohol common to the floral scents of numerous other plant species (Knudsen et al., 1993a; Kaiser, 1991). In addition to linalool, C. breweri flowers also synthesize and emit two linalool oxides, for which linalool is the proposed precursor (Winterhalter et al., 1986; Pichersky et al., 1994). The present inventor has previously observed S-linalool synthase (LIS) activity in Clarkia flower parts (Pichersky et al., 1994). This enzyme catalyzes the cation-dependent and stereoselective conversion of GPP to S-linalool (FIG. 1). LIS is both developmentally and differentially regulated in the various floral organs (Pichersky et al., 1994). Total LIS activity per flower was highest in petals, from which most of the linalool emission occurs. LIS activity per fresh weight was highest in stigma and style (i.e., the pistil), but most of the linalool produced by these tissues is converted to linalool oxides by as yet unidentified enzymes. Here the inventors report the purification and characterization of the S-linalool synthase from stigmata of C. breweri and the isolation and characterization of the cDNA gene encoding the S-linalool synthase.

GC- MS Characterization of C. breweri Volatiles

To determine the identity of the volatiles that give C. breweri flowers their odor, the technique of headspace scent collection has been used (Dobson, 1993), in which the scent of live flowers is collected and analyzed with a gas chromatograph/mass spectrometer. MS analysis is done on the peaks as they are eluted, and a computer data base containing several thousand mass spectra is automatically screened for matches. Using this technique, the a total of 12 compounds have been detected from two inbred lines of C. breweri plants. The monoterpene alcohol, linalool, and its trans-pyranoid oxide constituted major fractions of floral volatile output in both lines, as did the aromatic ester, benzyl acetate. The minor aroma constituents included linalool oxide (cis-furanoid), benzyl benzoate, eugenol, methyl salicylate and vanillin. Four additional compounds, isoeugenol, methyleugenol, methylisoeugenol and veratraldehyde were detected in all flowers from line 2 but were absent in plants from line 1. These 12 compounds fall into two groups, monoterpenes and aromatic compounds with a benzene skeleton.

In the present studies, abundant headspace compounds were collected from single, living flowers of C. breweri. No volatile compounds were detected from similar amounts of floral tissues of the closely related species, C. concinna, nor from other Clarkia species. When the headspace analyses were repeated with 20–30 living C. concinna flowers combined, the compounds linalool, pyranoid linalool oxide and furanoid linalool oxide were detected, but at levels 1000-fold less than in C. breweri. No benzenoid compounds were detected in C. concinna floral headspace collections.

Developmental and Temporal Variation in Monoterpene Emission by Whole Flowers

To determine the amount of monoterpenes emitted at different stages of floral development, headspace collection was begun with buds on the evening before they opened and ended 6 days later, after flowers had been pollinated and then wilted and abscised. The results indicate that emission of linalool and linalool oxides by C. breweri begins as soon as the flowers are open or, in the case of the pyranoid linalool oxide, even slightly before, and reaches a peak on Day 2

(D2). Emission of linalool was the highest, peaking at 49 µg/g fresh weight/12 h. Emission of the pyranoid linalool oxide peaked at 32 µg/g/12 hr. The furanoid linalool oxide was emitted at much lower level, peaking at 2.2 µg/g/12 h. Emission gradually declines after D2 until approximately 24 h after pollination (D3–5), when the flowers drastically decrease their monoterpene output. This cessation coincides with the general senescence of the flower. During the lifespan of the flower, marked variation in monoterpene emission between the day and night periods was not observed. Headspace collections made at 6 h intervals also failed to detect such changes. Diurnal variation has been previously described in some species (Matile et al., 1988; Overland, 1960) but not in others (Loughrin et al., 1990; Loughrin et al., 1991).

Localization and Quantification of Monoterpene Emission from the Different Parts of the Flower To determine the specific parts of the C. breweri flowers that emit monoterpenes, living flowers were modified by selectively excising floral parts, so that only one class of major floral organs (petals, stamens, or style) remained attached to the hypanthium and sepals. Headspace volatiles were then collected from these modified flowers over a 24 h period. The results show that ⅔ of the floral emission of linalool comes from petals, with the style contributing most of the rest. Emission of linalool per fresh weight is actually higher in the style than in petals, but because the total fresh weight of the style accounts for only 10% of the total mass of the flower while the petals account for 40%, the petal contribution is predominant. On the other hand, the style is responsible for nearly 100% of emission of the linalool oxides. Sepals, hypanthium and ovaries did not emit monoterpenes. In C. concinna, whose flowers emit monoterpenes at a level of 0.1% compared with C. breweri (per flower), that emission occurs only from styles. When the emissions of the different floral parts of C. breweri were added up, the result closely approximated the complete floral scent both qualitatively and quantitatively, indicating that each part is autonomous, and therefore synthesis of scent components must occur at the site of emission.

Determination of the level of the monoterpenes found in the flower and bud tissue indicates that there is a substantial pool of these compounds in the tissue. For example, at the time of peak emission (D2), the amount of linalool in the tissue is approximately equal to 10% of the total emitted over the corresponding 12 h period. Similar results were found for the linalool oxides. The observations that large pools of these monoterpenes exist within the tissues and that the changes in intracellular monoterpenes concentration parallel those of monoterpene emission (as does enzyme activity), suggest that these compounds are not sequestered for long as free monoterpenes inside the cell prior to the onset of emission. These observations differ from those made in Jasminum species, in which Watanabe et al. (1993) reported that fragrances were stored as non-volatile glycosides. However, Loughrin et al. (1992) found that the level of glycosidically bound volatiles in Nicotiana species was not correlated with the emission levels of such volatiles but with the age of the flower; older, senescing flowers had higher levels of stored glycosides.

Initial Characterization of Linalool Synthase

LIS activity was assayed by combining crude extract with $^3$H-GPP (or other substrates) in a buffer containing co-factors. LIS activity was monitored by counting the radioactive linalool extracted from the assay buffer with hexane (GPP is not soluble in hexane) in a scintillation counter. Radio-GC analyses (Croteau et al., 1990) were also undertaken because GPP could be enzymatically hydrolyzed by non-specific phosphatases to produce geraniol, or the tissue might contain other monoterpene synthases, and geraniol or the other monoterpenes that may be produced are also soluble in the organic phase. The studies indicated that crude extracts of open C. breweri flowers contained substantial amount of soluble LIS activity and no other monoterpene synthases, since the only labeled compound found in the hexane fraction was linalool. LIS activity was found to require $Mn^{2+}$ as a cofactor and GPP as the only substrate. Furthermore, with a special stereo-GC column it was also shown that the product of the reaction is exclusively S-linalool.

Linalool Synthase Activity in Flower Parts

To determine the site of, and temporal variation in, linalool synthesis, LIS activity was tested in crude extracts from different parts of flowers and from different stages of development. The results indicate that each flower part that emits linalool also contains significant LIS activity. This observation gives further support to the conclusion that linalool is emitted at or near the site of synthesis. However, there are pronounced differences among floral tissues. The highest and second highest levels of LIS activity per fresh weight were found in the stigma and pistil, respectively, whereas LIS activity in petals was only 20% of LIS activity in stigma at peak time (D1–D2), and activity in stamens was even lower. However, because petals constitute the bulk of the flower, they also possess the highest total amount of LIS activity per flower, which is consistent with the observation that petals emit the highest total amount of linalool per flower.

The level of LIS activity is also positively correlated with the rates of linalool emission. Both linalool emission and LIS activity in the petals peak at the D1–D2 period, and as LIS activity decreases afterwards, so does linalool emission. There is some low level of LIS activity in petals of unopened flowers, and some linalool is made in the buds, but apparently not in sufficient amounts to be volatilized. Stigmata and pistils displayed relatively low levels of linalool emission (which is nonetheless also positively correlated with LIS activity) but substantial emission of linalool oxides. Taken together with the observation of high levels of LIS activity in stigmata and pistils, it is contemplated that most of the linalool produced in these organs is converted into linalool oxides.

Interestingly, a low amount of LIS activity (0.1% compared with C. breweri flowers and 3% on a per fresh stigma weight basis) was found in the stigma but not in any other parts of C. concinna. Consistent with this observation, emission of linalool and linalool oxides has been found to occur, in trace amounts, only from the stigma of C. concinna. The interspecific hybrids, which are somewhat scented, have LIS activity level in the stigma that is 42% that found in C. breweri stigma, but their petal LIS activity is only 11% of C. breweri. Thus, the Lis gene is not unique to C. breweri, but is found, and is active, in C. concinna. This finding raises the question of the finction of the pathway in non-scented plants. In a few cases, linalool production in vegetative tissue in response to insect damage has been observed (Turlings et al., 1992), and it is contemplated that this compound may be used by the plants in such a response. It is contemplated, therefore, that the genes and proteins of the present invention may be useful in the protection of plants from insect damage.

Purification and Characterization of LIS

After characterizing the expression of LIS in floral parts throughout the development of the flower, a chromatographical purification protocol was developed that employed anion exchange (DE52) column, HAP column, and another ion-exchange column, FPLC's Mono-Q. As a starting material, a crude extract was prepared from 50 g of stigma tissue (derived from about 20,000 stigmata). The stigmata was used because they have the highest specific activity of is LIS (subsequently, LIS was also partially purified from petals, and it appears to be an identical protein). After Mono-Q chromatography, the fraction containing the peak LIS activity had a single protein, as judged by SDS-PAGE and silver staining. The LIS protein was calculated to have a molecular weight of app. 83 kDa from its migration in the gel. On a molecular sieving column, LIS activity elutes at about 70 kDa, indicating that LIS is active as a monomer. N-terminal sequencing of LIS eluted from Mono-Q gave a clear sequence (with initial yield>50%) indicating no heterogeneity in the purified enzyme (22 residues were determined). In addition, the sequences of several internal fragments were determined.

Cloning a Lis cDNA from *C. breweri*

In preparation for cloning the Lis gene, mRNA was isolated from petals and stigmata and cDNA expression libraries were prepared in the lambda-ZapII vector (Stratagene, Inc.) Several peptide sequences were used to construct oligonucleotides for PCR (polymerase chain reaction) using DNA obtained from the cDNA libraries. Fragments in the expected size range were obtained and analyzed.

Confirmation of Isolated cDNA Clones of Lis

The identity of the clones is determined in several ways. First, the oligonucleotide PCR probes are used as sequencing primers to determine the nucleotide sequence of adjacent regions in the clones. Because only parts of the amino acid sequences which had been obtained are used in the design of the oligonucleotides (7–8 residues out of 20–25 residues per peptide sequence), complete concordance of the predicted amino acid sequence obtained from the nucleotide sequence of the clones with the peptide sequences is a strong validation of the clones.

Clones that have the correct sequences are further tested by RFLP mapping (McGrath et al., 1993a; McGrath et al., 1993b; Pichersky et al., 1987a; Pichersky et al., 1987b; Pichersky et al., 1988; Pichersky et al., 1989; Pichersky et al., 1991). $F_1$ hybrids between *C. breweri* and *C. concinna* are used to obtain $F_2$s and $F_1$ X *C. concinna* backcross progeny. These plants are analyzed for emission of linalool and other volatiles. The trait of linalool emission is somewhat quantitative, but two distinct classes of strong emitters and non-emitters are clearly evident. Although the quantitative nature of the trait complicates the genetic analysis, the working hypothesis is that for a progeny to be a strong linalool emitter it has to have inherited the *C. breweri* version of the Lis gene, and therefore the putative Lis cDNA clones are used as probes to carry out Southern blots of $F_2$ and backcross progeny DNA to look for co-segregation of the *C. breweri* Lis allele with the trait of strong linalool emission. Additional proof of the clone being Lis is obtained by expressing the Lis cDNA in *E. coli* from the pET T7 promoter and producing antibodies to the protein. The antibodies are then shown to inhibit Lis activity from stigma extracts.

Final positive proof of the identity of Lis clones is obtained by expressing full-length cDNAs in *E. coli* and testing the proteins thus produced for enzyme activity. The preferred expression vector is pET, based on the T7 polymerase and promoter system (Studier et al., 1990).

Characterization of Lis Expression and its Regulation

The results indicate that LIS activity in the stigma and petals of *C. breweri* is substantial, whereas LIS activity in the stigma of *C. concinna* is 3% that of the corresponding *C. breweri* tissue (per fresh weight) and non-detectable in petals. Thus, linalool emission by *C. breweri* flowers is correlated with greater than a 30-fold or more increase of LIS activity in *C. breweri* flowers. Because the partially purified *C. breweri* petal LIS is essentially identical in its molecular and enzymatic properties to the stigma protein, and so is the *C. concinna* stigma LIS enzyme, the differences in the levels of LIS activity among *C. breweri* stigma, petals, and *C. concinna* stigma are not believed to be due to changes in turn-over number or other kinetic parameters of the enzyme. On the other hand, these differences are strongly correlated with the differences in the amount of protein. Thus, it appears that *C. breweri* has evolved the ability to make (and emit) greater amounts of monoterpenes by increasing the level of Lis gene transcription and/or increasing translational efficiency.

Expression levels of the Lis gene in stigma and petals in the two species may be determined by first determining the steady-state level of the mRNA with the Northern blotting technique, using the Lis cDNA clone as a probe, and also by primer extension, a technique that also allows the determination of the start of transcription (Kellman et al., 1990; Kellman et al., 1993; Piechulla et al., 1991). Run-on transcription assays may also be used to measures rates of transcription (Giuliana et al., 1988b). A correlation is then sought between transcription rates and steady-state mRNA levels, and between steady-state mRNA and LIS activity levels. Higher or lower levels than expected of MRNA compared with transcription rate suggests post-transcriptional control, and a discrepancy between steady-state MRNA level and LIS activity suggests translational or post-translation regulation as well, such as protein stability differences.

The nucleic acid segments of the present invention may also be used to isolate and characterize the Lis genes from various tissues in both species by screening genomic libraries constructed in the lambda vector EMBL3. In light of the present discovery, the promoter region of the *C. breweri* Lis gene may now be characterized by in vivo methods, such as reporter gene constructs, for example, and used for tissue specific expression of foreign genes. This may be done by the use of a promoterless reporter gene, GUS (Jefferson, 1987), to which the Lis promoter, intact or truncated, may be fused. Several constructs may be made, each missing a certain part of the Lis promoter. These constructs would preferably be used to transform *Nicotiana tabacum* SR1 plants, using the binary vector system of the Ti plasmid of *Agrobacterium tumefaciens* (An et al., 1986). Plants are regenerated, and optimal sequences for various promoter functions may thus be identified by the effect that their removal has on GUS activity (visualized by the addition of the GUS substrate to detached whole or sectioned organs).

Cellular and Subcellular Localization of LIS

The cellular and intracellular location of monoterpene synthesis is of considerable interest. In some plants that produce monoterpenes as defense compounds, special structures, such as leaf trichomes or resin glands (in stem tissue) have evolved where monoterpene synthesis takes place (Gershenzon et al., 1993; Lewinsohn et al., 1991). Neither light microscopy nor electron scanning microscopy has detected any specialized floral structures such as papillate cells or granular trichomes (see Stern et al., 1987) that could be responsible for volatile production or emission.

To determine which types of cells within a tissue such as the stigma contain Lis mRNA, the in situ hybridization technique may be used (Cox et al., 1988). The use of this technique is necessary because in plants, different types of cells may exist in a one-layer region and they cannot easily be separated in amounts large enough to extract mRNA. The present invention allows one to perform immunofluorescence assays (Baskin et al., 1992) using anti-LIS antibodies disclosed herein.

Antibodies

In another aspect, the present invention comprises an antibody that is immunoreactive with a linalool synthase polypeptide. An antibody can be a polyclonal or a monoclonal antibody and is preferably a monoclonal antibody. Means for preparing and characterizing antibodies are well known in the art (See, e.g., Antibodies "A Laboratory Manual, E. Howell and D. Lane, Cold Spring Harbor Laboratory, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

To obtain monoclonal antibodies, one would also initially immunize an experimental animal, often preferably a mouse, with an LIS composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the LIS polypeptide.

Following immunization, spleen cells are removed and fused, using a standard fusion protocol (see, e.g., The Cold Spring Harbor Manual for Hybridoma Development, incorporated herein by reference) with plasmacytoma cells to produce hybridomas secreting monoclonal antibodies against LIS. Hybridomas which produce monoclonal antibodies to the selected antigens are identified using standard techniques, such as ELISA and Western blot methods.

It is proposed that monoclonal antibodies specific to the particular LIS enzyme may be utilized in immunoabsorbent protocols to purify native or recombinant LIS enzyme species or variants thereof.

In general, both poly- and monoclonal antibodies against LIS may be used in a variety of embodiments. For example, they may be employed in antibody cloning protocols to obtain cDNAs or genes encoding LIS or related proteins. They may also be used in inhibition studies to analyze the effects of LIS in particular cells or tissue types. A particularly useful application of such antibodies is in purifying native or recombinant LIS, for example, using an antibody affinity column, or screening for Lis expressing cells. The operation of all such immunological techniques will be known to those of skill in the art in light of the present disclosure.

Biological Functional Equivalents

Modification and changes may be made in the structure of the encoded polypeptides used in the vectors and nucleic acid segments of the present invention and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the following codon table:

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the linalool synthase proteins, or corresponding DNA sequences which encode said proteins without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique may employ a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting, as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Localization of Monoterpene Emission and LIS Activity

Plant Material, Growth Conditions, Headspace Collection, GC-MS Analysis

Details of *C. breweri* and *C. concinna* stocks and growing conditions, dynamic headspace collection on Tenax and activated charcoal sorbents, and chemical analyses via GC-MS are as described in Raguso and Pichersky (1995). All headspace collections were performed in a Conviron growth chamber under a 12 h light/12 h dark photoperiod. Temperature was set to 25° C. during the light period and 18° C. during the dark period. In all experiments, headspace collections from ambient air and from vegetative tissues were used as controls.

Time Course of Scent Production

Volatile monoterpenoid production in individual flowers of four separate plants was monitored over a 7 d period beginning on the day before anthesis and continuing until floral abscission. Headspace volatiles were collected as described in Raguso and Pichersky (1995). The collections were made at 12 h intervals, corresponding to the dark and light periods in the growth chamber. All flowers were hand-pollinated with a cotton swab on the evening of day 3 after anthesis in order to simulate the typical life cycle of a *C. breweri* flower.

Localization and Quantification of Monoterpene Synthesis in Floral Parts

The specific floral parts responsible for scent emission were determined and the emission levels were quantified by collection of headspace volatiles from attached, second day (hermaphroditic) intact flowers and from same-stage flowers in which floral organs had been systematically removed, to leave only petals, only anthers or only the style. In order to detect all volatiles emitted by a given flower part, which could possibly emit different compounds at different times, a 24 h collection period was used. To determine diurnal variation in the emission of a given compound, headspace collections were taken over 6 and 12 hr intervals.

Monoterpene Extraction

Whole flowers representing the phenological spectrum from anthesis to abscission were excised at the base of the hypanthium, weighed and macerated with a glass rod in 1 mL of HPLC-grade hexane at ambient temperature, then stored in the dark at −20° C. Samples were concentrated to a volume of 75 $\mu$L under a flow of gaseous $N_2$ and 15 $\mu$L of a 0.3% (v/v) solution of geraniol in hexane were added as an internal standard. Four $\mu$l of each sample were then used for GC-MS analysis.

Linalool Synthase Enzyme Extraction and Assay

Enzyme extraction

A crude protein extract was prepared by macerating flower parts in a microcentrifuge tube in the presence of ice-cold buffer (10 volumes:fresh weight) containing 50 mM BisTris-HCl pH 6.9, 10 mM DTT, 5 mM $Na_2S_2O_5$, 1% (w/v) PVP-40 and 10% (v/v) glycerol. The slurry was centrifuged for 10 min and the supernatant transferred to a new tube. For each time point, extracts of 3 to 5 flowers from 3 different plants were combined.

Enzyme Assay and Product Analysis

Linalool synthase activity was assayed by diluting 10 $\mu$L of crude extract (1.5–3 $\mu$g protein) into 80 $\mu$L of assay buffer (50 mM potassium HEPES pH 7.8, 5 mM DTT, 5 mM sodium metabisulfite, 10% (v/v) glycerol, 20 mM $MgCl_2$ and 5 mM $MnCl_2$ [Lewinsohn et al., 1991]), adding 10 $\mu$L of [1-$^3$H]-GPP to final concentration 16 $\mu$M, at 150 mCi/mol [substrate synthesized according to Croteau and Cane (1985) ], and overlaying the mixture with either pentane or hexane to trap volatile metabolites. The tube was then vortexed briefly and incubated at 20° C. for 1 h. Appropriate controls included the omission of crude extract, the use of boiled crude extracts, the omission of substrate and/or cations, and the substitution of other potential substrates such as (3R)- and (3S)-[1-$^3$H]-linalyl pyrophosphate.

After 1 h, the tube was vortexed again and the amount of the radioactive linalool product, which partitioned into the organic phase, was determined by an LSC of an aliquot. Radio-GC analysis (Croteau and Satterwhite, 1990) of labeled products in the organic phase was also undertaken to examine the formation of geraniol (liberated from the substrate by phosphatases) and to determine whether other monoterpene synthases were present in the extracts. These radio-GC analyses showed that no floral tissue contained detectable monoterpene synthase activity other than LIS (linalool>95% of product by coincidence of radioactivity with authentic standard), and that only crude extracts from mature pollen grains contained appreciable phosphatase activity. Because of the presence of phosphatases in the pollen grains, anther tapeta were routinely excluded in the preparation of subsequent cell-free extracts.

Temporal Variation in Scent Emission by Intact Flowers

Under the present growing conditions, the first buds become visible on the *C. breweri* plant 4–6 weeks after germination. The closed buds develop for approximately 12–18 d before the fused sepals split and reflex, allowing the petals to open (anthesis). Anthesis in *C. breweri* typically occurs in the morning. Flowers that have been pollinated at any time after Day 2 past anthesis, when stigma lobes recurve and become receptive, will begin to wilt within 24 h of pollen deposition. After 6–7 d, unpollinated flowers also begin to senesce and wilt. The present inventor has previously shown (Raguso and Pichersky, 1995) that three monoterpenes—linalool, furanoid linalool oxide and pyranoid linalool oxide—are constituents of the scent of *C. breweri* flowers. In order to determine the amount of monoterpenes emitted at different stages of floral development, time-course headspace collections were performed at 12 h intervals, followed by GC-MS analysis. Headspace collection was performed with buds on the evening before they opened and ended 6 d later, after flowers had been pollinated and then wilted and abscised.

Unopened flowers (buds) emitted no linalool or furanoid linalool oxide, but they did emit small amounts of pyranoid linalool oxide. Significant emission of all three monoterpenes began at anthesis and peaked during Day 2, and afterwards began a gradual decline. Monoterpene emission was still high on the evening of Day 4, 24 h after hand pollination, and then rapidly declined. Overall, the emission of linalool by the intact flowers was higher than the corresponding oxides, peaking at 8.5 $\mu$g/flower/12 h. Emission of the pyranoid linalool oxide peaked at 5.9 $\mu$g/flower/12 h. The furanoid linalool oxide was emitted at much lower level, peaking at 0.4 $\mu$g/flower/12 h. Senescence (wilting) of all flowers was observed by the morning of Day 5, yet low levels of linalool and linalool oxides were emitted until abscission on the evening of Day 6.

Quantitation of Monoterpenes in Flower Tissue

The amounts of monoterpenes in intact flowers at different developmental stages were determined by hexane extraction and GC-MS analysis. The three monoterpenes were detectable in mature buds 2–3 d from anthesis. Tissue levels of linalool peaked on the evening of Day 2 and then declined, paralleling the pattern found for linalool emission. The maximal level of linalool found in the flower tissue was approximately 10% of the amount of linalool emitted by the flower over a 12 h period. Tissue levels of linalool oxides peaked at Day 3, while the emission of linalool oxides was highest at Day 2. On Day 2, levels of linalool oxides in the tissue constituted approximately 10% of the emission levels of these compounds over a 12 h period, but on Day 3 this ratio increased to 20% to 60%.

Localization and Quantification of Monoterpene Emission from the Different Parts of the Flower

*C. breweri* flowers

To determine the specific parts of the *C. breweri* flowers that emit monoterpenes, studies were performed in which living flowers were modified by selectively excising floral parts, so that only one class of major floral organ (petals, stamens, pistil) remained attached to the hypanthium and sepals. Headspace volatiles were then collected from these modified flowers over a 24 h period. The data obtained were used to calculate the contribution of each part to the total emission of the flower (Table 2), and also the emission of each part relative to its weight (Table 3). These data revealed that the majority of the linalool emission came from the petals, although substantial emission was also detected from the pistil (⅓ of the amount emitted by the petals) and some linalool was emitted by the stamens (¹⁄₁₀ of the petal emission). On the other hand, pyranoid linalool oxide and furanoid linalool oxide were emitted almost exclusively by the pistil.

*C. concinna* flowers

*C. concinna*, a close relative of *C. breweri*, has flowers which are smaller and which do not emit a detectable scent. A previous investigation revealed that *C. concinna* flowers do emit low levels of linalool and linalool oxides (0.1% of emission compared with *C. breweri*) (Raguso and Pichersky, 1995). The levels of emission of these monoterpenes in floral organs of *C. concinna* (Tables I,II) were then examined. The results indicate that volatile emission occurs only in pistils.

Linalool Synthase Activity in Flower Parts

Linalool synthase activity in flowers

To determine the site of synthesis of linalool and the temporal variation in its synthesis, crude extracts were prepared from different parts of the flowers that had been open for 1 to 6 days and these extracts were assayed for activity of linalool synthase, the enzyme that catalyzes the conversion of GPP to linalool. In these studies, the flower was dissected into smaller parts than was possible in the headspace collection of modified live flowers detailed above. For example, in the headspace collection it was not logistically possible to measure the contribution of the stigma separately from that of the rest of the pistil. However, in preparing crude extracts from different parts of the flower this limitation was overcome.

LIS activity was found in several parts of the flowers. At the peak of LIS activity, at Days 1–2, total LIS activity was similar in petals and pistil (stigma+style). However, stigmata possessed the highest level of LIS activity per fresh weight, followed by style tissue (with 25–35% of the specific activity found in stigma), petals (20% of stigma LIS specific activity at peak time) and stamens. None of the remaining floral parts—sepals, hypanthium and ovaries—were found to contain any LIS activity. The vegetative parts of the plant were also devoid of LIS activity.

Levels of LIS activity varied during the lifespan of the flower in concert with the levels of linalool emission and its concentration in floral tissue. Maximal LIS activity was observed during Days 1–2. When flowers were pollinated on Day 3, LIS activity decreased by 90% in the stigma and 50% in the petals within 48 h, similar to the reduction in monoterpene emission following pollination. However, when pollination did not occur, LIS activity in the different floral organs declined only slowly from the peak levels over the next few days.

Linalool synthase activity in buds

Since freshly opened flowers already contain substantial enzyme activity, the level of LIS activity was investigated in buds. In order to carry out these studies, it was necessary to devise a method to classify stages in bud development. Due to variation in bud size and naturation time within and among plants, it was difficult to predict the exact number of days remaining before anthesis by bud size alone. However, in contrast to bud size, color changes during the development of the petals and stigma were found- a progression from white to dark purple—to be reliable markers for the developmental stage of the bud. These indicators were used to denote five stages in bud development. Each stage lasts approximately 2–3 days, for a total of 12–18 days preceding anthesis. In addition, because the small size of some floral organs within buds precluded obtaining enough material for enzyme assays, only petals and pistils were examined for LIS activity. Whereas the youngest buds (stages 1 and 2) had no detectable LIS activity, pistils (but not petals) of third stage buds already possessed appreciable LIS activity (approximately 30% of peak level). By stage 5, levels of LIS activity in the petals were close to or at the peak levels found in petals of open flowers.

Linalool synthase activity in flowers of *C. concinna*

The LIS activity in extracts of *C. concinna* flower parts of Day 2 flowers was examined. Consistent with the emission data (Tables I,II), LIS activity was detected only in the stigma, which had a level of activity of 2.8 fkat/stigma (and per flower) and 4.6 fkat/g fresh weight. These levels are respectively 0.3% of the LIS activity per stigma (0.01% per flower) and 3% per fresh weight of activity in *C. breweri* stigmata of the equivalent stage.

Temporal Variation in Scent Production by Whole Flowers and Buds

The strong, sweet floral scent of *C. breweri* is unique in its genus, and is correlated with pollination by moths, a mode of reproduction that is novel among Clarkia species (MacSwain et al., 1973). Emission of the monoterpene components of the scent begins as soon as the flowers are open and reaches a peak on Day 2. During the lifespan of the flower, marked variation in monoterpene emission between the day and night periods was not observed. It is possible that temporary, but substantial, increases or decreases in emission were missed because of their short duration, but headspace collections made at 6 h intervals also failed to detect such changes, and samples did not vary by more than a factor of 1.5. Daily cycling in emission of linalool and other floral scent components, with a nocturnal peak in intensity coinciding with periods of moth activity, is a feature of many moth-pollinated flowers, such as *Cestrum nocturnum* (Solanaceae) (Overland, 1960; Matille and Altenberger, 1988). However, in other moth-pollinated flowers, such as *Nicotiana sylvestris* (Solanaceae), rates of linalool emission do not differ appreciably between night and day (Loughrin et al., 1990, 1991).

Localization and Quantification of Monoterpene Emission from the Different Parts of the Flower The data (Table 2) show that ⅔ of the floral emission of linalool comes from petals, with the style contributing most of the rest. Emission of linalool per fresh weight is actually higher in the pistil than in petals (Table 3), but because the total fresh weight of the pistil accounts for only 10% of the total mass of the flower while the petals account for 40% (Table 4), the petal contribution is predominant. On the other hand, the pistil is responsible for nearly 100% of floral emission of the linalool oxides. When the emissions of the different floral parts are added up, the results closely approximate the complete floral scent both qualitatively and quantitatively, indicating that each part is autonomous and thus syntheses of scent components occur at the sites of emission. Previous studies (Dobson et al., 1990; Knudsen and Tollsten, 1991) also found that different parts of flowers emit different relative amounts of scent components, although absolute quantities were not reported.

The observations that relatively small pools of free monoterpenes exist within the tissues, and that the changes in tissue monoterpene concentrations parallel those of monoterpene emission suggest that these compounds are not appreciably sequestered as free monoterpenes inside the cell prior to the onset of emission but are emitted as soon as they are made. The absence of both appreciable pools of scent volatiles and the biosynthetic enzymes of such compounds in mature floral tissue of Jasminum species prompted Watanabe et al. (1993) to discover that fragrance components were stored as non-volatile glycosides. However, Loughrin et al. (1992) found that the level of glycosidically bound volatiles in Nicotiana species was not correlated with the emission levels of such volatiles but with the age of the flower; older, senescing flowers had higher levels of stored glycosides. The presence of glycosidically bound monoterpenes in Clarkia flowers has not yet been examined. However, the presence in mature *C. breweri* flowers of LIS and, likely, the other enzymes in the pathway suggests that if such stored, modified monoterpenes are present, they might not contribute to scent emission, or their contribution might not be essential.

Linalool Synthase Activity in Flower Parts

The highest and second highest levels of LIS activity per fresh weight were found in the stigma and style, respectively. The pistil is the only part of the flower (excluding the ovaries) that continues to increase in size and weight after the flower opens, but its specific LIS activity does not decrease, indicating that additional LIS activity accrues there, at least during the first few days after anthesis. However, the petals constitute the bulk of the LIS-containing floral tissue (Table III), and they possess a similar or even higher total amount of LIS activity compared with the pistil. Each flower part that emits linalool or linalool oxides -petals, pistils and stamens—also contains significant LIS activity, whereas flower parts that do not contain LIS activity do not contain or emit these monoterpenes. These observations lend further support to the conclusion based on the determination of emission from flowers in which a single part was left that linalool and its oxides are emitted at or near the site of synthesis and that translocation is probably not of significance.

The levels of LIS activity in the different parts of the flower throughout the lifespan of the flower are also positively correlated with the rates of emission of linalool and the two linalool oxides. Both monoterpene emission and LIS activity in the petals, pistil and stamens peak during the first two days after anthesis, and as LIS activity decreases afterwards (especially after the flower has been pollinated), so do linalool and linalool oxides emissions. However, buds of later stages contain appreciable amounts of LIS activity but they do not accumulate or emit these monoterpenes. It is likely that earlier steps in the pathway are not yet operating in the buds, either for lack of other enzymes or because of sequestration of enzymes and/or substrates in different sub-cellular compartments. Alternatively, monoterpenes may be synthesized in buds of later stages but may be rapidly converted to other compounds or derivatives.

The pistil displayed relatively low levels of linalool emission but substantial emission of linalool oxides (Table 2). Taken together with the observation of high levels of LIS activity in stigma and style, the conclusion is inescapable that most of the linalool produced in these organs is converted into linalool oxides. Winterhalter et al. (1986) presented evidence that, in papaya tissues, the linalool oxides are synthesized from linalool via 6,7-epoxylinalool as an intermediate (FIG. 1). They further showed that the conversion of linalool to 6,7-epoxylinalool was enzymatically catalyzed, although a specific enzyme was not identified. The enzyme(s) responsible for the formation of the linalool oxides from 6,7-epoxylinalool, if such exist, have also not yet been identified.

Interestingly, a low amount of LIS activity (0.1% compared with C. breweri flowers and 3% on a per fresh stigma weight basis) is found in the stigma but not in any other parts of the flowers of C. concinna, a species that has no discernable floral scent (Raguso and Pichersky, 1995) and is not pollinated by moths (MacSwain et al., 1973). However, linalool and both linalool oxides have been detected, albeit in trace amounts, in the headspace of flowers of C. concinna (0.1% of that of C. breweri) (Table I and Raguso and Pichersky, 1995), and this emission has now been traced to the pistil (Tables 2, 3). The observation that LIS activity and monoterpene synthesis occur in the pistil of an essentially non-scented flower raises the possibility that linalool and/or the linalool oxides may have some physiological function in this organ which is unrelated to attracting pollinators.

TABLE 2

Emission of Monoterpenes from Flower Parts of C. breweri and C. concinna; 24 h Collection Beginning on d 2

| Species | Linalool μg | % total | Pyranoid Linalool Oxide μg | % total | Furanoid Linalool Oxide μg | % total |
|---|---|---|---|---|---|---|
| C. breweri | | | | | | |
| Stamens (n = 5) | 1.31 ± 0.59 | 5.60 | 0.01 ± 0.01 | 0.02 | 0.00 ± 0.01 | 0.42 |
| Pistil (n = 8) | 4.78 ± 2.84 | 20.30 | 29.44 ± 5.35 | 129.00 | 0.62 ± 0.12 | 52.00 |
| Petals (n = 7) | 14.08 ± 4.01 | 60.25 | 0.09 ± 0.05 | 0.40 | ND[a] | ND |
| Whole flowers (n = 23) | 23.37 ± 1.72 | 100.00 | 22.74 ± 1.61 | 100.00 | 1.19 ± 0.13 | 100.00 |
| C. concinna | | | | | | |
| Stamens (n = 3) | ND | ND | ND | ND | ND | ND |
| Pistil (n = 3) | 0.024 ± 0.002 | 100.00 | 0.028 ± 0.001 | 100.00 | 0.001 ± 0.001 | 100.00 |
| Petals (n = 3) | ND | ND | ND | ND | ND | ND |
| Whole flowers (n = 3) | 0.024 ± 0.002 | 100.00 | 0.03 ± 0.001 | 100.00 | 0.001 ± 0.001 | 100.00 |

[a]ND, Not detected.

TABLE 3

Emission of Monoterpenes from Flower Parts of C. breweri and C. concinna; 24 h Collection Beginning on d 2

| Species | Linalool | Pyranoid Linalool Oxide | Furanoid Linalool Oxide |
|---|---|---|---|
| C. breweri | | | |
| Stamens (n = 5) | 54.5 ± 24.4 | 0.2 ± 0.2 | 0.2 ± 0.2 |
| Pistil (n = 8) | 296.0 ± 177.6 | 1840.0 ± 334.5 | 39.0 ± 7.7 |
| Petals (n = 7) | 220.0 ± 62.7 | 1.4 ± 0.8 | ND[a] |
| C. concinna | | | |
| Stamens (n = 3) | ND | ND | ND |
| Pistil (n = 3) | 8.1 ± 0.8 | 9.4 ± 0.4 | 0.3 ± 0.2 |
| Petals (n = 3) | ND | ND | ND |

[a]ND, Not detected.

TABLE 4

Weight Distribution in Different Parts of the C. breweri Flower

| Flower Part | Total Wt mg | Percent of Total |
| --- | --- | --- |
| Stamens | 24.0 ± 2.0 | 15.1 |
| Pistil | 16.0 ± 3.0 | 10.1 |
| Stigma | 6.0 ± 0.5 | 3.8 |
| Style | 10.0 ± 0.7 | 6.3 |
| Petals | 64.0 ± 1.0 | 40.2 |
| Hypanthium and sepals | 55.0 ± 7.0 | 34.6 |
| Whole flower (without ovaries) | 159.0 ± 8.0 | 100.0 |

EXAMPLE 2

Purification and Characterization of S-Linalool Synthase

Plant Materials, Substrates and Reagents

Details of C. breweri stocks and growing conditions are described in Raguso and Pichersky (1995). Stigmata from freshly opened flowers (not more than 2 days after anthesis) were used for enzyme isolation, as this tissue has been shown to contain very high levels of LIS per gram of tissue (Pichersky et al., 1994). S-linalool was purified from coriander oil, and R-linalool was from Ho wood (both from Berje Chemical Products, Long Island City, N.Y.). [1-$^3$H]-GPP, and 3R- and 3S-[1-$^3$H]-LPP were synthesized as previously described (Croteau et al., 1994).

Enzyme Extraction

All steps were carried out at 4° C. Crude protein extracts were prepared by homogenizing freshly excised stigmata in a chilled mortar in the presence of ice-cold buffer (10:1 (v/w) buffer:tissue) containing 50 mM potassium BisTris, pH 6.9, 10 mM dithiothreitol, 5 mM Na$_2$S$_2$O$_5$, 1% (w/v) polyvinylpyrrolidone (Sigma, PVP-40) and 10% (v/v) glycerol. The slurry was passed through miracloth and centrifuged for 10 min at 12,000 g to produce a supernatant that contained the bulk of the LIS activity.

Enzyme Purification

The crude extract (100 ml) was loaded onto a DEAE-cellulose (0.7 cm diam.×6 cm) column (Whatman, DE52) that was pre-equilibrated with a solution containing 50 mM BisTris, pH 6.9, 10% glycerol and 10 mM DTT (buffer A) at a flow rate of about 1 ml/min. Following elution of the unadsorbed material, the column was washed with 50 ml of buffer A followed by an additional 20 ml of buffer A containing 150 mM KCl. LIS activity was then eluted with 20 ml of buffer A containing 250 mM KCl. Fractions with the highest LIS activity (about 60% yield, 10 ml), were either pooled and used immediately, or frozen at −20° C. for up to 1 month with less than 20% loss of activity. The DEAE-cellulose purified fractions were diluted 2-fold with ice-cold buffer A, and loaded on a 1 cm diam.×10 cm hydroxyapatite column (Bio-Gel HT, Bio-Rad, Richmond, Calif.) installed in a Pharmacia FPLC apparatus, and pre-equilibrated with 100 ml of buffer A, at a flow rate of 0.5 ml/min. After the enzyme was loaded, the column was washed with 20 ml buffer A and then eluted using a linear gradient (100 ml) from 0 to 200 mM Na-phosphate in buffer A. The fractions containing LIS activity, eluting at about 100 mM Na-phosphate, were pooled (10 to 16 ml) and loaded on a pre-packed Pharmacia Mono-Q HR 5/5 FPLC column equilibrated with buffer A. After a 20-ml wash with buffer A, a steep linear gradient from 0 to 100 mM KCl in buffer A (10 ml) was applied, followed by a more gradual linear gradient from 100 to 400 mM KCl in buffer A (100 ml, 0.25 ml/min). The enzyme consistently eluted at about 220 mM KCl. After dialysis to assay conditions, the enzyme at this level of purity was used for characterization.

Gel Permeation Chromatography and SDS-PAGE

A Superdex 75 Hi Load 16/60 column (Pharmacia FPLC) was employed to determine the native molecular mass of the C. breweri linalool synthase. Hydroxyapatite-purified linalool synthase (1 ml, 44.1 pkat/mg protein) was loaded on the Superdex 75 column and eluted with buffer A containing 5 mM DTT, using a flow rate of 1 ml/min. Two-ml fractions were collected. Protein standards of known molecular mass (Sigma, St. Louis, Mo.) were used for calibration. For SDS-PAGE, the method of Laemmli (Laemmli, 1970) was employed, with 10% acrylamide and a ratio of 30:0.8 w/w acrylamide:bis-acrylamide. Gels were stained with Coomassie Brilliant Blue G (Andrews, 1986) or silver (Blum et al., 1987). The molecular weight marker proteins were from BioRad (Richmond, Calif.).

Enzyme assay

LIS activity was determined by mixing 10 μl of the enzyme sample with 12 μM [1-$^3$H]-GPP (s.a. 150 Ci/mol) in 100 μl of assay buffer (50 mM Hepes-KOH, pH 7.8, 10 mM DTT, 5 mM Na$_2$S$_2$O$_5$, 10% (v/v) glycerol, 20 mM MgCl$_2$ and 5 mM MnCl$_2$ (Lewinsohn et al., 1991) and, as an overlay to trap volatiles, either 1 ml hexane (for scintillation counting) or 2 ml of pentane (for radio-GC analysis). The mixture was then vortexed briefly, centrifuged to separate phases (5 sec. Eppendorf) and incubated at 20° C. without shaking for up to 1 h (higher temperatures resulted in elevated rates of chemical conversion of GPP to various alcohols, including linalool). After incubation, the assay mixture was briefly mixed again to extract non-polar products into the organic layer. An 800-μl aliquot of the hexane phase was placed into a scintillation vial containing 10 ml of a cocktail of 0.4% (w/v) Omnifluor (Du Pont, Boston Mass.) dissolved in 30% (v/v) ethanol in toluene and counted in a Packard TriCarb 460 CD scintillation spectrometer (efficiency for $^3$H=36%) to determine the total monoterpene synthase activity. To examine in detail the products formed, radio-GC was performed as described (Croteau et al., 1990). For this purpose, the 2 ml pentane extract containing the enzymatically formed $^3$H-labeled products was removed, dried by passage through MgSO$_4$, and internal standards were added (10 μg each of linalool and geraniol; nerol was UD also included in initial experiments). The mixture was then concentrated to ~10 μl under a gentle stream of nitrogen, and an aliquot (2–3 μl) was injected into a Gow-Mac 550P radio gas chromatograph fitted with a 0.125 in ×12 ft stainless steel column loaded with AT-1000 (Gas Chrom Q, Alltech), attached to a Packard 894 gas proportional counter. The initial column temperature was 170° C. and, following a 5 min hold, was programmed at 5° C./min to 220° C., using He at a flow rate of 50 ml/min. Control incubations included the omission of enzyme extract, the use of boiled enzyme extract, the omission of substrate, and the omission of divalent cations. All of these controls produced negligible radioactivity in the hexane phase of the enzyme assay mixtures.

Protein

Protein was determined by the method of Bradford (Bradford, 1976), using bovine serum albumin as standard.

Stereochemical Analyses

The enantiomeric composition of linalool samples was determined on a fused silica capillary column (0.25 mm internal diam.×30 m) coated with a 0.25 μm film of β-cyclodextrin (J & W Scientific, Cyclodex B), operated at an initial temperature of 75° C. for 15 min followed by a rise of 5° C./min to 200° C. $H_2$ at a head pressure of 13.5 psi was used as carrier gas (Alonso et al., 1992).

Results

Figure 2:
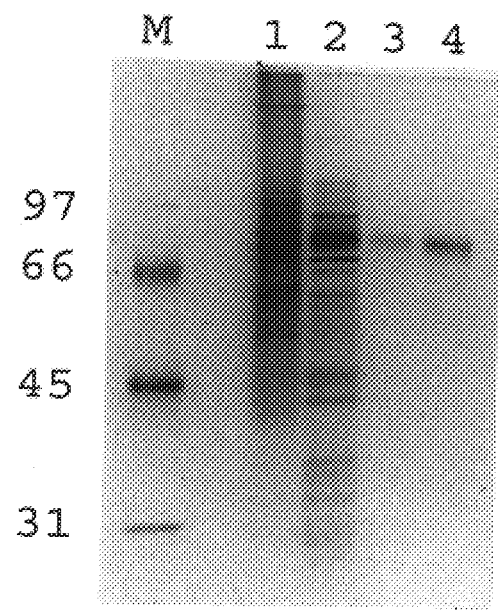
FIG. 2. SDS-PAGE analysis of S-linalool synthase throughout purification. M=molecular weight markers (numbers at left indicate kDa). 1. Sample after DEAE-cellulose chromatography (16 μg protein); 2. Sample after hydroxyapatite chromatography (8 μg protein); 3. After Mono Q anion exchange FPLC (1 μg protein); 4. Same as in lane 3 but 2 μg protein. The gel was Coomassie-stained as described in Andrews, 1986.

Flower stigmata were used as the enzyme source, as they contained very high enzyme activity levels (147 fkat/mg Fr.Wt.) (Pichersky et al., 1994) (See Example 1). A representative purification scheme for the C. breweri S-linalool synthase is shown in Table 5. Typically, 10 g Fr.Wt. of freshly excised stigmata gave 140 μg of pure linalool synthase following the initial DEAE-cellulose and hydroxyapatite chromatography steps (to remove low molecular weight pigments and phenolic materials that severely interfered with later FPLC steps), and Mono Q chromatography (FIG. 2). SDS-PAGE analysis of many of the purified Mono Q preparations revealed the presence of a single protein band corresponding to a molecular mass of about 79±3 Kda. The N-terminal amino acid sequence of this protein matched the sequence encoded by a LIS cDNA clone. In some preparations, a minor protein band slightly smaller than LIS was also visible (FIG. 2 lanes 3, 4). However, the elution profile of this band from the Mono Q column did not coincide with the peak of LIS activity, and its N-terminal sequence did not match that predicted from the LIS clone. Thus, after attaining a 26-fold purification, accompanied by 9% recovery, a greater than 95% homogeneous preparation was obtained, due in large part to the high specific activity of the starting material and the rapid and gentle fractionation protocol. Only a single peak of linalool synthase activity was observed in each step of the purification.

Figure 3:
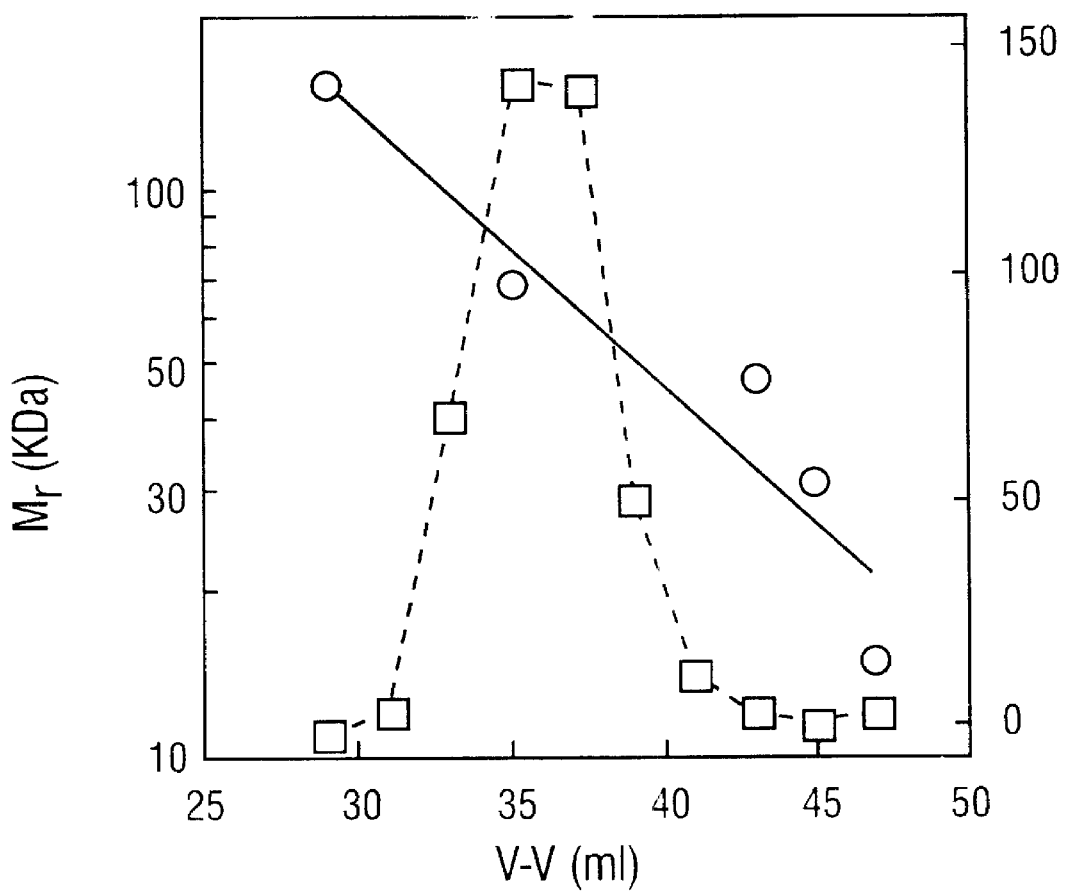
FIG. 3. Gel permeation chromatography of the C. breweri S-linalool synthase. The Mono Q purified enzyme was separated on a Superdex 75 (Pharmacia FPLC), and gave a molecular mass corresponding to 73±5 kDa by comparison with protein standards: yeast alcohol dehydrogenase ($M_r$ 150,000), bovine serum albumin ($M_r$ 67,000), hen egg white ovalbumin ($M_r$ 45,000), bovine carbonic anhydrase ($M_r$ 29,000) and lysozyme ($M_r$ 14,500).

The native molecular mass of linalool synthase activity was determined to be about 73±5 KDa based on co-elution with bovine serum albumin on gel permeation chromatography and comparison of the elution volume to those of known proteins (FIG. 3). Based on a subunit mass of 79 KDa determined by SDS-PAGE (FIG. 2) and a native molecular size of 73 KDa indicated by gel permeation chromatography (FIG. 3), linalool synthase is thought to be a monomer of 76±3 KDa. Other monoterpene synthases from higher plants are active monomers in the 50–70 KDa range (Alonso, 1992; Lewinsohn et al., 1992b), or homodimers with 40–50 KDa subunits (Gambliel et al., 1984).

Figure 4A:
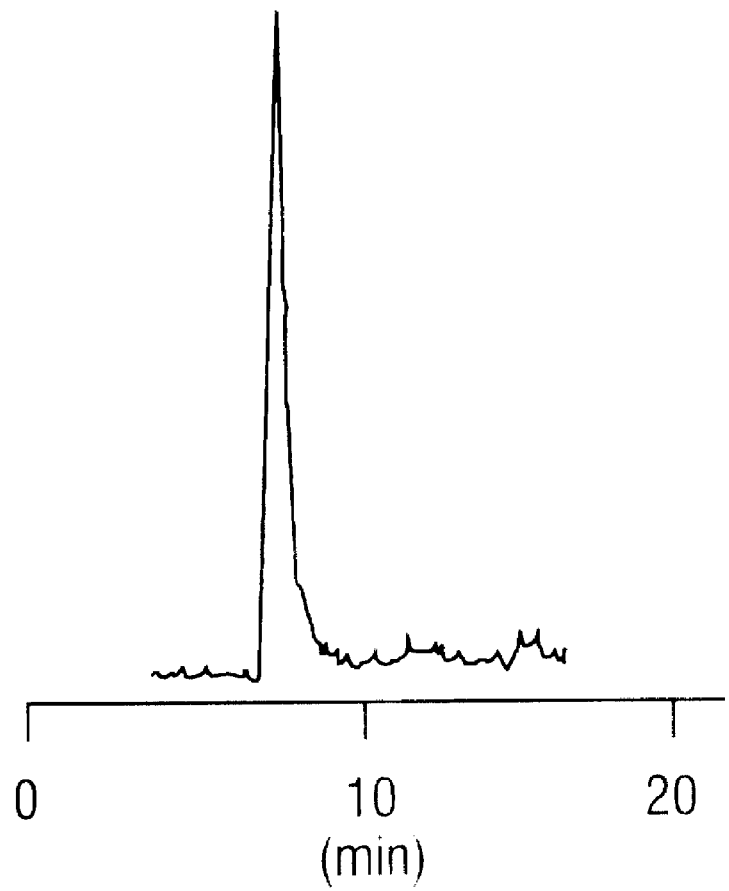
FIG. 4. Capillary radio-GC analysis of the product of S-linalool synthase. The tracing in A is the radioactivity response to the pentane-soluble products generated by incubating C. breweri S-linalool synthase preparation with [$^3$H]-GPP. The tracing in B is the thermal conductivity detector response to authentic geraniol and linalool standards.
Figure 4B:
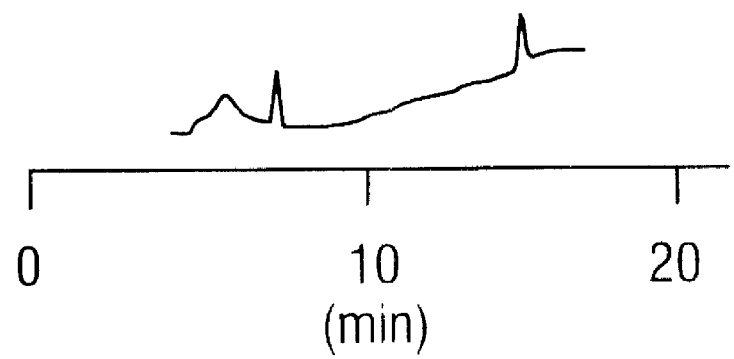

Radio-GLC analysis of the products generated by extracts of C. breweri stigmata (FIG. 4) or petals that had been incubated with [$^3$H]-GPP indicated the presence of linalool only. The preparations were devoid of other monoterpene synthase activities or GPP phosphohydrolase activity as evidenced by the absence of [$^3$H]-geraniol in the reaction products. In contrast, C. breweri leaves contained only GPP phosphohydrolase activity, as leaf-derived cell-free extracts produced only geraniol. The enantiomer compositions of the linalool emitted by C. breweri flowers (obtained by head space collection [Raguso and Pichersky, 1995]), and that produced in vitro from GPP by the purified enzyme from stigmata were next determined by their separation on a β-cyclodextrin capillary column. Both samples contained only the 3S-antipode of linalool.

The conversion of GPP to cyclohexanoid monoterpenes is thought to involve an initial ionization step followed by collapse of the resulting ion pair (1) to enzyme-bound LPP, which after transoid to cisoid rotation, ionizes to promote the cyclization step (FIG. I) (Croteau, 1987). LPP can serve as an alternate substrate for most monoterpene synthases and is generally more efficient than GPP since the isomerization is commonly the rate-limiting step of the coupled reaction sequence (Croteau et al., 1994; Rajaonarivony et al., 1992).

To determine whether C. breweri LIS accepts LPP as an alternate substrate, both the R- and the S-linalyl enantiomers were tested as precursors (Table 6). Only a low rate of conversion of S-LPP to linalool was observed (15% the rate for GPP), whereas the R- antipode was essentially not converted to linalool. This suggests that in the normal reaction the ionization of GPP leads to capture by water of the resulting cation (1) at the tertiary center to give linalool directly without the involvement of LPP. Thus the reaction catalyzed by LIS is considerably simpler than the coupled isomerization-cyclization sequence catalyzed by monoterpene cyclases (FIG. I).

Similar to other monoterpene synthases (Alonso, 1992; Lewinsohn et al., 1992; Rajaonarivony et al., 1992; Alonso et al., 1993), S-linalool synthase requires a divalent metal ion for activity. $Mn^{2+}$ is most efficient ($K_m$=45 μM), although $Mg^{2+}$ ($K_m$=330 μM) can substitute for $Mn^{2+}$ at half the rate. Neither $Cu^{2+}$, $Zn^{2+}$, $Ca^{2+}$, nor $Co^{2+}$ (at 1 to 10 mM, as the chloride salts) support the enzymatic reaction, and no detectable linalool is formed in the absence of divalent metal ions.

A $K_m$ value of 0.9 μM was calculated for GPP from a Lineweaver-Burk plot. This value is in the range determined for other monoterpene synthases from plants (Alonso et al., 1992; Alonso et al., 1993). A turnover number of 31.6 $sec^{-1}$ was calculated for LIS under saturating conditions, indicating that the enzyme is much faster than other monoterpene synthases examined so far (Alonso et al., 1992; Alonso et al., 1993). A broad pH optimum of 7.4 was calculated for the enzyme, with the rates at pH 6.4 and 8.4 being ~80% of the optimal. This optimal pH range is similar to those determined for other monoterpene synthases (Alonso et al., 1992; Lewinsohn et al., 1992; Alonso et al., 1993). Similar rates were observed while substituting Hepes buffer with Tris-HCl. The enzyme is unstable in the absence of DTT (>95% loss over 2 h at 4° C.), and its later addition does not result in the regaining of activity. Addition of the non-ionic detergent Triton-X-100 (0.1% w/v) had no effect on enzyme activity, but similar levels of sodium dodecyl sulfate resulted in a complete loss of activity. Similarly to other monoterpene synthases (Lewinsohn et al., 1991; Wheeler et al., 1986), the enzyme is very stable to vigorous vortexing in the presence of non-polar organic solvents such as hexane and pentane.

TABLE 5

Purification of C. breweri Linalool Synthase

| Purification Step | Protein (mg) | Activity (pkat) | Specific Activity (pkat $mg^{-1}$) | Recovery (%) | Purification Fold |
|---|---|---|---|---|---|
| Crude extract[a] | 39.6 | 604 | 15.2 | 100 | 1 |
| DEAE-cellulose | 15.4 | 342 | 22.2 | 56.6 | 1.5 |
| Hydroxyapatite | 4.6 | 203 | 44.1 | 33.6 | 2.9 |
| Mono Q | 0.14 | 55.3 | 395 | 9.2 | 26.0 |

[a]The starting material was 10 g of excised stigmata (approx. 2500–300 stigmata).

TABLE 6

Substrate Specificity of Purified *C. breweri* Linalool Synthase

| Substrate[a] | Rate[b] |
| --- | --- |
| [1-$^3$H]Geranyl pyrophosphate | 100 ± 9.6 |
| 3R-[1-$^3$H]Linalyl pyrophosphate | 0.6 ± 0.6 |
| 3S-[1-$^3$H]Linalyl pyrophosphate | 15.1 ± 6.0 |

[a]Putative substrates tested at 12 µM.
[b]Rates of 100% with [1-$^3$H]GPP are relative to 22. 2 pkat/mg protein. Averages and SE's of four replicate determinations.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alonso, W. R., and Croteau, R. (1993) in Methods in Plant Biochemistry (Enzymes of Secondary Metabolism) (Lea, P. J. Ed), pp. 239–260, Academic Press, London.

Alonso, W. R., Rajaonarivony J. I. M., Gershenzon, J., and Croteau, R. (1992) *J. Biol. Chem.* 267, 7582–7587.

An, G., Watson, B. D. and Chiang, C. C. (1992) Plant Physiol 81:301–395.

Andrews, A. T. (1986) Electrophoresis: Theory, Techniques and Biochemical and Clinical Applications, Oxford Univ. Press (Clarendon), London/New York.

Baskin, T. I., Busby, C. H., Fowke, L. C., Sammut, M., and Gubler, F. (1992) Planta 187:405–413.

Bevan, M., Barnes, W. M., Chilton, M. D. (1983) Nucleic Acid Research. 11:369–385.

Blum, H., Beier, H., and Gross, H. J. (1987) Electrophoresis 8, 93–99.

Bouchez D., Tokluhisa J. G., Llewellyn D. J., Dennis E. S. and Ellis J. G. (1989) EMBO Journal 8(13):4197–4204.

Bradford, M. M. (1976) *Anal. Biochem.* 72, 248–254.

Callis, J., Fromm, M., Walbot, V. (1987) Genes and Develop. 1:1183–1200.

Chandler, V. L., Radicella, J. P., Robbins, P. P., Chen, J., Turks, D. (1989) The Plant Cell 1:1175–1183.

Conkling, M. A., Cheng, C. L., Yamamoto, Y. T., Goodman, H. M. (1990) Plant Physiol. 93:1203–1211.

Cox, K. H., Goldberg, R. B. (1988) In: Plant Molecular Biology: A Practical Approach. Shaw, C. H. ed. Oxford:IRL Press, pp 1–35.

Craig, S., Czaplewski, L. G., Edwards, R. M., Gilbert, R. J., and Hunter, M. G., WO 9313206, Jul. 8, 1993.

Cristou P., McCabe D. E., Swain W. F. (1988) Plant Physiol 87:671–674.

Croteau, R., Alonso, W. R., Koepp, A. E., and Johnson, M. A. (1994) *Arch. Biochem. Biophys.* 309, 184–192.

Croteau R, Satterwhite D M (1990) Methods for radiocapillary gas chromatography employing a modified oxidation-reductive train and flow-through detector. J Chromatogr 500: 349–354.

Croteau, R. (1987) Chem. Rev. 87, 929–954.

Croteau R, Cane D E (1985) Monoterpenes and sesquiterpene cyclases. Meth Enzymol 110: 383–405.

Croteau R, Karp F (1991) Origin of Natural Odorants. Ch. 4, pp 101–126 in Muller P, Lamparsky D, eds, "Perfume: art, science and technology", Elsevier Appl Sci, Inc. NY.

Croteau R (1986) Biochemistry of monoterpenes and sesquiterpenes of the essential oils. In Herbs, Spices and Medicinal Plants; Recent Advances in Botany, Horticulture and Pharmacology (Cracker L E, Simon J E, edsm vol 1, Oryx Press, Phoenix, p 81–133.

Dawson, F. A. (1994) Naval Stores Review, March/April, 6–12.

Dobson HEM (1993) Floral Volatiles in Insect Biology, in Bernays E (ed) Insect-Plant Interactions, Vol V. pp 47–81. CRC Press, Boca Raton.

Dobson HEM, Bergstrom G, Groth I (1990) Differences in fragrance chemistry between flower parts of *Rosa rugosa* Thunb. (Rosaceae). Israel J Bot 39:143–156.

Dodson C, Dressler R, Hills H, Adams R, Williams N (1969) Biologically active compounds in orchid fragrances. Science 164: 1243–1249.

Ebert, P. R., Ha, S. B., An. G. (1987) PNAS 84:5745–5749.

Ellis J. G., Llewellyn D. J., Walker J. C., Dennis E. S., and Peacock W. J. (1987) EMBO Journal 6(11):3203–3208.

Forde, B. G. (1994) Results Probl Cell Differ. 20:87–103.

Fromm, H., Katagiri, F., Chua, N. H. (1989) The Plant Cell 1:977–984.

Galen C (1985) Regulation of seed set in *Polemonium viscosum*: floral scents, pollination and resources. Ecology 66: 792–797.

Galen C, Kevan P (1983) Bumblebee foraging and floral scent dirnorphism: *Bombus kirbyellus* and *Polemonium viscosum*. Canad J Zool 61: 1207–1213.

Gallie, D. R., Lucas, W. J., Walbot, V. (1989) The Plant Cell 1:301–311.

Gambliel H, Croteau R (1982) Biosynthesis of (±)-α-pinene and (±)-β-pinene from geranyl pyrophosphate by a soluble enzyme system from sage (*Salvia officinalis*). J Biol Chem 257: 2335–2342.

Gambliel, H., and Croteau, R. (1984) *J. Biol. Chem.* 259, 740–748.

Gelvin, S. B., Schilperoort, R. A., Varma, D. P. S., eds. Plant Molecular Biology Manual (1990).

Gershenzon J, Croteau R (1993) Terpenoid biosynthesis: the basic pathway and formation of monoterpenes, sesquiterpenes, and diterpenes. In Moore Jr TS (ed) Lipid metabolism in Plants. CRC Press, Boca Raton Fla. pp 339–388.

Gijzen, M., Lewinsohn, E., Savage, T. J. and Croteau, R. B. (1993) in Bioactive Volatile Compounds from Plants. (Teranishi, R., Buttery, R. J. and Sugisawa, H. Eds.) pp. 8–22. ACS Symposium Series 525. Washington D.C.

Giuliano, G., Hoffman, N. E., Ko, K., Scolnik, P. A., Cashmore, A. R. (1988) EMBO J. 7:3635–3642.

Harborne J. B. (1991) in Ecological Chemistry and Biochemistry of Plant Terpenoids (Harborne J. B., Tomes-Barberan F. A. Eds.) pp. 399–426, Clarendon Press, London.

Hemleben, V., and Zentgraph, U. (1994) *Results Probl Cell Differ*. 20:3–24.

Hudspeth, R. L. and J. W. Grula. (1989) Plant Mol. Biol. 12:579–589.

Jefferson, R. A. (1987) Plant Mol Biol Rep 5:387–405.

Joulain D (1987) The composition of the headspace from fragrant flowers: further results. Flavour and Fragrances J 2: 149–155.

Kaiser R (1991) Trapping, investigation and reconstitution of flower scents. Ch 7, pp 213–248 in Muller P, Lamparsky D (eds), "Perfume: Art, Science and Technology", Elsevier Appl Sci, Inc, NY.

Kellmann, J. W., Pichersky, E., Piechulla, B., (1990) Photobiology and Photochemistry 52:35–41.

Kellmann J., Wiesse, M., Pichersky, E., Piechulla, B. (1993) Mol Gen Genet 237:439–448.

Knudsen, J. T., and Tollsten, L. (1993) *Bot. J. Linn. Soc.* 113, 263–284.

Knudsen JT, Tollsten L (1991) Floral scent and intrafloral scent differentiation in Moneses and Pyrola (Pyrolaceae). Plant Syst Evol 177: 81–91.

Knudsen J T, Tollsten L, Bergstrom G (1993) Floral scents—a checklist of volatile compounds isolated by head-space techniques. Phytochemistry 33: 253–280.

Kyte, J. and Doolittle, R. F. (1982) J. Mol. Biol., 157(1):105–132.

Laemmli, U. K. (1970) *Nature* (London) 227, 680–685.

Langenheim, J. H. (1994) *J. Chem. Ecol.* 20, 1223–1280.

Lawton, M. A., Tierney, M. A., Nakamura, I., Anderson, E., Komeda, Y., Dube, P., Hoffman, N., Fraley, R. T., Beachy, R. N. (1987) Plant Mol. Biol. 9:315–324.

Lewinsohn, E., Gijzen, M. and Croteau, R. B. (1992) in Regulation of Isopentenoid Metabolism (Nes, W. D., Parish, E. J. and Trzaskos, J. M. Eds.) pp. 8–17, ACS Symposium Series 497. Washington D.C.

Lewinsohn E, Gijzen M, Croteau R (1992) Wound-inducible pinene cyclases from grand fir: purification, characterization and renaturation after SDS-PAGE. Arch Biochem Biophys 293: 167–173.

Lewinsohn E, Gijzen M, Savage T J, Croteau R (1991) Defense mechanisms in conifers. Relationship of monoterpene cyclase activity to anatomical specialization and oleoresin monoterpene content. Plant Physiol 96: 38–43.

Loughrin J, Hamilton-Kemp T, Burton H R, Andersen R A, Hildebrand D F (1992) Glycosidically bound volatile components of *Nicotiana sylvestris* and *N. suaveolens* flowers. Phytochemistry 31: 1537–1540.

Loughrin J, Hamilton-Kemp T, Andersen R A, Hildebrand D F (1990) Volatiles from flowers of *Nicotiana sylvestris, N. otophora* and *Malus X domestica*: headspace components and day/night changes in their relative concentrations. Phytochemistry 29: 2473–2477.

Loughrin J, Hamilton-Kemp T, Andersen R, Hildebrand D (1991) Circadian rhythm of volatile emission from flowers of *Nicotiana sylvestris* and *N. suaveolens*. Physiol Plant 83: 492–496.

MacSwain J, Raven P, Thorp R (1973) Comparative behavior of bees and Onagraceae. IV. Clarkia bees of the western United States. Univ of Calif Publ Ent 70: 1–80.

Matile P, Altenburger R (1988) Rhythms of fragrance emission in flowers. Planta 174: 242–247.

McGrath, J. M., Hickok, L., Pichersky, E. (1993) Plant Syst Evol 189:203–210.

McGrath, J. M., Jansco M., Pichersky, E. (1993) Theor Appl Genet 86:880–888.

Nagai, K., Thogersen, H. C. (1987) Methods in Enzymology 153:461–481.

Odell, J. T., Nagy, F., Chua, N. H. (1985) Nature 313:810–812.

Omirulleh, S, Abraham, M., Golovkin, M., Stefanov, I., Karabaev, M. K., Mustardy, L., Morocz, S., Dudits, D. (1993) Plant Molecular Biology 21:415–428.

Overland L (1960) Endogenous rhythm in opening and odor of the flowers of Cestrum nocturnum. Am J Bot 47: 378–382.

Pellmyr O (1986) Three pollination morphs in Cimicifuga simplex: incipient speciation due to inferiority in competition. Oecologia 78: 304–307.

Pichersky, E., Raguso, R. A., Lewinsohn, E., and Croteau, R. (1994) Plant Physiol. 106:1533–1540.

Pichersky, E., Logsdon, J., McGrath, J. M., Stasys, R. A. (1991) Mol Gen Genet 225:453–458.

Pichersky, E., Brock, T. G., Nguyen, D., Hoffinan, N. E., Piechulla, B., Tanksley, S. D., Green, B. (1989) Plant Mol Biol 12:257–270.

Pichersky, E., Tanksley, S. D., Piechulla B., Stayton, M. M., Dunsmuir, P. (1988) Plant Mol Biol 11:69–71.

Pichersky, E., Hoffnan, N. E., Malik, V. S., Bernatzky, R., Tanksley, S. D., Szabo, L., Cashmore, A. R. (1987) Plant Mol Biol 9:109–120.

Pichersky, E., Hoffman, N. E., Bernatzky, R., Piechulla, B., Tanksley, S. D., Cashmore, A. R. (1987) Plant MOl Biol 9:205–216.

Piechulla, B., Kellmann, J., Pichersky, E., Schwartz, E., Forster, H. H., (1991) Mol Gen Genet 230:413–422.

Raguso R A, Pichersky E (1995) Floral volatiles from *Clarkia breweri* and *C. concinna* (Onagraceae): recent evolution of floral scent and moth pollination. Plant Sys Evol, 194:55–67.

Rajaonarivony J I M, Gershenzon J, Croteau R (1992) Characterization and mechanism of (4S)-limonene synthase, a monoterpene cyclase from the glandular trichomes of peppermint (*Mentha X piperita*). Arch Biochem Biophys 296: 49–57.

Rajaonarivony, J. I. M, Gershenzon, J., and Croteau, R. (1992) *Arch. Biochem. Biophys.* 296, 49–57.

Sambrook, J., Fritsch, E. F., and Maniatus, T. (1989) Molecular Cloning, A Laboratory Manual 2nd ed.

Stern W, Curry K, Pridgeon A (1987) Osmophores of Stanhopea (Orchidaceae). Am J Bot 74: 1323–1331.

Studier, F. W., Rosenberg, A. H., Dunn, J. J. (1990) Methods in Enzymology 185:60–89.

Sullivan, T. et al. (1989) Mol. Gen. Genet 215:431–440.

Tabor, S., Richardson, C. C. (1985) Proc Natl Acad Sci (USA) 82:1074–1078.

Turlings, T. C. J., Tumlinson, J. H. (1992) Proc Natl Acad Sci (USA) 89:8399–8402.

Turlings, T. C. J., Tumlinson, J. H., and Lewis, W. J. (1990) Science 250, 1251–1253.

Vasil, V., Clancy, M., Ferl, R. J., Vasil, I. K., Hannah, L. C. (1989) Plant Physiol. 91:1575–1579.

Walker, J. C., Howard, E. A., Dennis, E. S., Peacock, W. J. (1987) PNAS 84:6624–6628.

Wang, Y., Zhang, W., Cao, J., McEhoy, D. and Ray Wu. (1992) Molecular and Cellular Biology 12:3399–3406.

Watanabe N, Watanabe S, Nakajima R, Moon J H, Shimokihira K, Inagaki J, Etoh H, Asai T, Sakata K, Ina K (1993) Formation of flower fragrance compounds from their precursors by enzymic action during flower opening. Biosci Biotech Biochem 57: 1101–1106.

Wheeler, C. J., and Croteau, R. (1986) *Arch. Biochem. Biophys*. 248, 429–434.

Wilmink A; van de Ven BC; Dons JJ. (1995) *Plant Mol Biol* (NETHERLANDS) 28, 949–55.

Winterhalter, P., Katzenberger, D., and Schreier, P. (1986) *Phytochemistry* 25, 1347–1350.

Winterhalter P, Katzenberger D, Schreier P (1986) 6,7-epoxy-linalool and related oxygenated terpenoids from *Carica papaya* fruit. Phytochemistry 25: 1347–1350.

Yang, N. S., Russell, D. (1990) PNAS 87:4144–4148.

What is claimed is:

1. An isolated nucleic acid segment comprising a nucleic acid sequence encoding a linalool synthase protein or polypeptide.

2. The isolated nucleic acid segment of claim 1, wherein said nucleic acid sequence encodes the amino acid sequence of SEQ ID NO:2.

3. The nucleic acid segment of claim 1, wherein said nucleic acid segment is positioned under the control of a promoter.

4. The nucleic acid segment of claim 1, wherein said nucleic acid segment is positioned under the control of a heterologous promoter.

5. A recombinant vector comprising the nucleic acid segment of claim 1.

6. A recombinant host cell comprising a nucleic acid segment in accordance with claim 1.

7. The nucleic acid segment of claim 2, wherein said nucleic acid segment comprises a nucleic acid sequence consisting of the nucleic acid sequence of SEQ ID NO:1 or a nucleic acid segment hybridizing to SEQ ID NO:1 under high stringency conditions of 0.02M–0.15M NaCl at temperatures of at least 50° C. to 70° C.

8. The recombinant vector of claim 5, wherein said vector is a recombinant expression vector which expresses a linalool synthase protein or polypeptide on introduction into a host cell.

9. The recombinant vector of claim 5, wherein said vector comprises a nucleic acid sequence having the sequence of SEQ ID NO:1.

10. The recombinant vector of claim 5, wherein the vector comprises the pBLUESCRIPT or pBIN19 nucleic acid sequence.

11. The recombinant host cell of claim 6, wherein the host cell is a prokaryotic cell.

12. The recombinant host cell of claim 6, wherein the host cell is a eukaryotic cell.

13. The recombinant host cell of claim 6, wherein the nucleic acid segment is positioned in a recombinant vector.

14. The nucleic acid segment of claim 7, wherein said nucleic acid segment has the nucleic acid sequence of SEQ ID NO:1.

15. A plant transformed with the recombinant expression vector of claim 8.

16. The recombinant host cell of claim 12, wherein the host cell is in a plant.

17. The recombinant host cell of claim 13, wherein the recombinant vector is a recombinant expression vector and the host cell expresses a linalool synthase polypeptide.

18. The recombinant host cell of claim 13, wherein the recombinant expression vector comprises a nucleic acid sequence having the sequence of SEQ ID NO:1.

19. An isolated nucleic acid segment which comprises a sequence of at least 15 contiguous nucleotides which corresponds to at least a 15 nucleotide contiguous sequence of SEQ ID NO:1 or its complement.

20. The nucleic acid segment of claim 19, further defined as comprising a sequence of at least 30 contiguous nucleotides which corresponds to a sequence of at least 30 contiguous nucleotides of SEQ ID NO:1 or its complement.

21. The nucleic acid segment of claim 19, further defined as a DNA segment.

22. The nucleic acid segment of claim 20, further defined as comprising a sequence of at least 50 contiguous nucleotides which corresponds to a sequence of at least 50 contiguous nucleotides of SEQ ID NO:1 or its complement.

23. The nucleic acid segment of claim 22, further defined as comprising a sequence of at least 100 contiguous nucleotides which corresponds to a sequence of at least 100 contiguous nucleotides of SEQ ID NO:1 or its complement.

24. The nucleic acid segment of claim 23, further defined as comprising a sequence of at least 200 contiguous nucleotides which corresponds to a sequence of at least 200 contiguous nucleotides of SEQ ID NO:1 or its complement.

25. The nucleic acid segment of claim 24, further defined as comprising a sequence of at least 500 contiguous nucleotides which corresponds to a sequence of at least 500 contiguous nucleotides of SEQ ID NO:1 or its complement.

26. The nucleic acid segment of claim 25, further defined as comprising a sequence of at least 1,000 contiguous nucleotides which corresponds to a sequence of at least 1,000 contiguous nucleotides of SEQ ID NO:1 or its complement.

27. The nucleic acid segment of claim 26, further defined as comprising a sequence of at least 2,000 contiguous nucleotides which corresponds to a sequence of at least 2,000 contiguous nucleotides of SEQ ID NO:1 or its complement.

28. The nucleic acid segment of claim 27, further defined as comprising a sequence of at least 2,583 contiguous nucleotides which corresponds to a sequence of at least 2,583 contiguous nucleotides of SEQ ID NO:1 or its complement.

29. The nucleic acid segment of claim 28, further defined as comprising a sequence of at least 2,610 contiguous nucleotides which corresponds to a sequence of at least 2,610 contiguous nucleotides of SEQ ID NO:1 or its complement.

30. The nucleic acid segment of claim 29, further defined as comprising a sequence of at least 2,681 contiguous nucleotides which corresponds to the 2,681 nucleotide sequence of SEQ ID NO:1 or its complement.

31. A method of using a nucleic acid segment encoding a linalool synthase protein or polypeptide, comprising the steps of:

preparing a recombinant vector in which said nucleic acid segment is positioned under the control of a promoter;

introducing said recombinant vector into a host cell; and culturing said host cell under conditions effective to allow expression of the encoded linalool synthase protein or polypeptide.

32. The method of claim 31, further comprising the step of collecting said expressed linalool synthase protein or polypeptide.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
  ( A ) LENGTH: 2681 base pairs
  ( B ) TYPE: nucleic acid
  ( C ) STRANDEDNESS: single
  ( D ) TOPOLOGY: linear ( i x ) FEATURE:
  ( A ) NAME/KEY: CDS
  ( B ) LOCATION: 28..2637

( x i ) SEQUENCE DESCRIPTION: SEQ ID NO:1:

```
AACCAAACCA  CCTTAAACAA  GACAACC ATG CAG CTC ATA ACA AAT TTC TCC           51
                                Met Gln Leu Ile Thr Asn Phe Ser
                                 1               5

TCA TCA TCA TCA GAA TTG CAG TTT CTT GTG GAT AAG GTT AAG AGA GAA            99
Ser Ser Ser Ser Glu Leu Gln Phe Leu Val Asp Lys Val Lys Arg Glu
        10              15                  20

TCA TTG TCT TCT TCA TCA TCT AAT ACT CAG AAT TTG TTT CTC TCA ACT           147
Ser Leu Ser Ser Ser Ser Ser Asn Thr Gln Asn Leu Phe Leu Ser Thr
 25              30                  35                      40

TCA CCT TAT GAC ACT GCT TGG CTC GCC CTT ATC CCT CAT CCT CAT CAT           195
Ser Pro Tyr Asp Thr Ala Trp Leu Ala Leu Ile Pro His Pro His His
                45                  50                  55

CAC CAT CAC CAT GGC CGA CCC ATG TTT GAA AAA TGT CTG CAA TGG ATT           243
His His His His Gly Arg Pro Met Phe Glu Lys Cys Leu Gln Trp Ile
            60                  65                  70

CTC CAT AAC CAG ACA CCA CAA GGT TTC TGG GCA GCA GCT GGT GAC AAT           291
Leu His Asn Gln Thr Pro Gln Gly Phe Trp Ala Ala Ala Gly Asp Asn
                75                  80                  85

ATT TCC GAC ACC GAC GAT GAC GTC ACC CTG GAT TGT CTT CTA TCA ACC           339
Ile Ser Asp Thr Asp Asp Asp Val Thr Leu Asp Cys Leu Leu Ser Thr
        90                  95                 100

TTG GCT TGC TTA GTT GCA CTC AAA AGG TGG CAG CTT GCT CCC GAC ATG           387
Leu Ala Cys Leu Val Ala Leu Lys Arg Trp Gln Leu Ala Pro Asp Met
105             110                 115                 120

ATT CAT AAA GGA TTG GAA TTT GTA AAT AGA AAC ACA GAG AGA CTT GTA           435
Ile His Lys Gly Leu Glu Phe Val Asn Arg Asn Thr Glu Arg Leu Val
                125                 130                 135

ATG AAG CAG AAG CCG AGC GAC GTT CCT CGT TGG TTC ACC ATC ATG TTC           483
Met Lys Gln Lys Pro Ser Asp Val Pro Arg Trp Phe Thr Ile Met Phe
            140                 145                 150

CCG GCG ATG CTC GAG CTT GCC GGC GCT TCC AGT CTC CGA GTC GAT TTC           531
Pro Ala Met Leu Glu Leu Ala Gly Ala Ser Ser Leu Arg Val Asp Phe
                155                 160                 165

AGC GAG AAT CTT AAC AGA ATC TTG GTG GAA CTA TCT CAA AAT AGG GAT           579
Ser Glu Asn Leu Asn Arg Ile Leu Val Glu Leu Ser Gln Asn Arg Asp
        170                 175                 180

GAC ATT CTC ACA AGG GAG GAA GTT GAT GAG AAG AAG CAA TAC TCA CCA           627
Asp Ile Leu Thr Arg Glu Glu Val Asp Glu Lys Lys Gln Tyr Ser Pro
185             190                 195                 200

TTG CTA CTA TTT CTA GAA GCA TTG CCT GCA CAA TCC TAT GAC AAT GAT           675
Leu Leu Leu Phe Leu Glu Ala Leu Pro Ala Gln Ser Tyr Asp Asn Asp
                205                 210                 215

GTT CTA AAG CAA ATT ATA GAC AAG AAC TTG AGC AAT GAT GGT TCT TTA           723
Val Leu Lys Gln Ile Ile Asp Lys Asn Leu Ser Asn Asp Gly Ser Leu
```

|   |   |   |   |   |   |   |   |   |   |   |   |   |   |   |   |   |
|---|---|---|---|---|---|---|---|---|---|---|---|---|---|---|---|---|
|   |   |   | 220 |   |   |   |   | 225 |   |   |   |   | 230 |   |   |   |
| TTG | CAA | TCG | CCT | TCT | GCT | ACA | GCA | AGA | GCA | TAC | ATG | ATA | ACA | GGA | AAT | 771 |
| Leu | Gln | Ser | Pro | Ser | Ala | Thr | Ala | Arg | Ala | Tyr | Met | Ile | Thr | Gly | Asn |   |
|   |   | 235 |   |   |   | 240 |   |   |   | Tyr | Met | 245 |   |   |   |   |
| ACC | AGA | TGC | TTA | TCG | TAT | CTA | CAC | TCT | TTA | ACA | AAT | AGC | TGC | TCT | AAT | 819 |
| Thr | Arg | Cys | Leu | Ser | Tyr | Leu | His | Ser | Leu | Thr | Asn | Ser | Cys | Ser | Asn |   |
|   | 250 |   |   |   | 255 |   |   |   |   | 260 |   |   |   |   |   |   |
| GGA | GGA | GTA | CCA | TCA | TTC | TAT | CCT | GTT | GAC | GAC | GAC | CTC | CAT | GAT | CTT | 867 |
| Gly | Gly | Val | Pro | Ser | Phe | Tyr | Pro | Val | Asp | Asp | Asp | Leu | His | Asp | Leu |   |
| 265 |   |   |   |   | 270 |   |   |   |   | 275 |   |   |   |   | 280 |   |
| GTC | ATG | GTG | AAT | CAA | CTG | ACA | AGG | TCG | GGT | TTG | ACT | GAA | CAT | CTC | ATC | 915 |
| Val | Met | Val | Asn | Gln | Leu | Thr | Arg | Ser | Gly | Leu | Thr | Glu | His | Leu | Ile |   |
|   |   |   |   | 285 |   |   |   |   | 290 |   |   |   |   |   | 295 |   |
| CCG | GAG | ATT | GAC | CAC | CTT | CTA | CTC | AAA | GTT | CAA | AAG | AAC | TAC | AAA | TAC | 963 |
| Pro | Glu | Ile | Asp | His | Leu | Leu | Leu | Lys | Val | Gln | Lys | Asn | Tyr | Lys | Tyr |   |
|   |   |   | 300 |   |   |   |   | 305 |   |   |   |   | 310 |   |   |   |
| AAA | AAG | CAT | CAC | CAA | AAT | CAT | TGT | ATA | GCA | TTG | CTG | CGG | AAC | TAT | ACG | 1011 |
| Lys | Lys | His | His | Gln | Asn | His | Cys | Ile | Ala | Leu | Leu | Arg | Asn | Tyr | Thr |   |
|   |   | 315 |   |   |   |   | 320 |   |   |   |   | 325 |   |   |   |   |
| GGA | TTC | ATT | AGC | ATT | TTT | GGT | TGC | TTC | GAG | TCA | ATA | ATC | ACT | GGG | TAT | 1059 |
| Gly | Phe | Ile | Ser | Ile | Phe | Gly | Cys | Phe | Glu | Ser | Ile | Ile | Thr | Gly | Tyr |   |
| 330 |   |   |   |   | 335 |   |   |   |   |   |   | 340 |   |   |   |   |
| CAC | CAT | CAA | TTT | TTT | TGT | TGG | TTT | TTA | GAT | GAC | GAC | GAA | ATC | CGT | GAT | 1107 |
| His | His | Gln | Phe | Phe | Cys | Trp | Phe | Leu | Asp | Asp | Asp | Glu | Ile | Arg | Asp |   |
| 345 |   |   |   |   | 350 |   |   |   |   | 355 |   |   |   |   | 360 |   |
| CAC | ATC | GAA | ACA | AAC | TAC | GAG | GAA | TTT | GCT | GCC | GTG | CTT | CTT | AAT | GTG | 1155 |
| His | Ile | Glu | Thr | Asn | Tyr | Glu | Glu | Phe | Ala | Ala | Val | Leu | Leu | Asn | Val |   |
|   |   |   |   | 365 |   |   |   |   | 370 |   |   |   |   | 375 |   |   |
| TAT | CGA | GCT | ACC | GAT | CTT | ATG | TTC | TCC | GGC | GAA | GTC | CAA | CTT | GTC | GAA | 1203 |
| Tyr | Arg | Ala | Thr | Asp | Leu | Met | Phe | Ser | Gly | Glu | Val | Gln | Leu | Val | Glu |   |
|   |   |   | 380 |   |   |   |   | 385 |   |   |   |   | 390 |   |   |   |
| GCA | AGA | TCT | TTC | GCT | ACC | AAG | AAT | CTT | GAG | AAA | ATA | TTA | GCA | ACA | GGA | 1251 |
| Ala | Arg | Ser | Phe | Ala | Thr | Lys | Asn | Leu | Glu | Lys | Ile | Leu | Ala | Thr | Gly |   |
|   |   | 395 |   |   |   | 400 |   |   |   |   | 405 |   |   |   |   |   |
| AAC | ATA | CAT | AAA | ACT | AAT | GCA | GAT | ATC | TCA | TCT | AGT | TTG | CAT | AAG | ATG | 1299 |
| Asn | Ile | His | Lys | Thr | Asn | Ala | Asp | Ile | Ser | Ser | Ser | Leu | His | Lys | Met |   |
| 410 |   |   |   |   | 415 |   |   |   |   | 420 |   |   |   |   |   |   |
| ATC | GAA | CAC | GAA | CTA | AGA | GTT | CCT | TGG | ACC | GCA | AGA | ATG | GAC | CAT | GTT | 1347 |
| Ile | Glu | His | Glu | Leu | Arg | Val | Pro | Trp | Thr | Ala | Arg | Met | Asp | His | Val |   |
| 425 |   |   |   | 430 |   |   |   |   | 435 |   |   |   |   | 440 |   |   |
| GAA | AAT | CGA | ATT | TGG | ATC | GAA | GAA | ATA | GCT | TCC | AGT | GCT | TTA | TGG | TTT | 1395 |
| Glu | Asn | Arg | Ile | Trp | Ile | Glu | Glu | Ile | Ala | Ser | Ser | Ala | Leu | Trp | Phe |   |
|   |   |   |   | 445 |   |   |   | 450 |   |   |   |   | 455 |   |   |   |
| GGA | AAA | TCA | TCC | ATC | CTT | AGG | TTA | TCT | TGC | TTT | CAC | AAG | ATG | AGT | TTA | 1443 |
| Gly | Lys | Ser | Ser | Ile | Leu | Arg | Leu | Ser | Cys | Phe | His | Lys | Met | Ser | Leu |   |
|   |   | 460 |   |   |   | 465 |   |   |   | 470 |   |   |   |   |   |   |
| CAG | CAA | CTC | GCG | GTG | AAA | AAT | TAT | ACG | CTT | CGA | CAA | TTG | GTT | TAC | CGA | 1491 |
| Gln | Gln | Leu | Ala | Val | Lys | Asn | Tyr | Thr | Leu | Arg | Gln | Leu | Val | Tyr | Arg |   |
|   |   | 475 |   |   |   |   | 480 |   |   |   |   | 485 |   |   |   |   |
| GAC | GAG | CTT | GCG | GAA | GTT | GAG | AGG | TGG | TCT | AAA | GAA | AGA | GGG | CTA | TGT | 1539 |
| Asp | Glu | Leu | Ala | Glu | Val | Glu | Arg | Trp | Ser | Lys | Glu | Arg | Gly | Leu | Cys |   |
|   |   | 490 |   |   |   | 495 |   |   |   | 500 |   |   |   |   |   |   |
| GAC | ATG | GGA | TTT | TGT | AGA | GAG | AAA | ACC | GGG | TAT | TGT | TAC | TAC | GCA | TTT | 1587 |
| Asp | Met | Gly | Phe | Cys | Arg | Glu | Lys | Thr | Gly | Tyr | Cys | Tyr | Tyr | Ala | Phe |   |
| 505 |   |   |   |   | 510 |   |   |   |   | 515 |   |   |   |   | 520 |   |
| GCG | GCA | AGT | ACT | TGT | CTG | CCG | TGG | AGT | TCC | GAC | GTG | AGG | CTG | GTC | CTG | 1635 |
| Ala | Ala | Ser | Thr | Cys | Leu | Pro | Trp | Ser | Ser | Asp | Val | Arg | Leu | Val | Leu |   |
|   |   |   |   | 525 |   |   |   |   | 530 |   |   |   |   | 535 |   |   |
| ACC | AAG | GCG | GCA | GTT | GTC | ATT | ACA | GTG | GCC | GAT | GAT | TTC | TTT | GAT | GTC | 1683 |
| Thr | Lys | Ala | Ala | Val | Val | Ile | Thr | Val | Ala | Asp | Asp | Phe | Phe | Asp | Val |   |

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 540 |     |     |     |     | 545 |     |     |     |     | 550 |     |     |      |
| GAA | GGA | TCT | ATG | GTT | GAT | CTC | GAA | AAA | TTA | ACG | GAT | GCA | GTT | CGG | AGG | 1731 |
| Glu | Gly | Ser | Met | Val | Asp | Leu | Glu | Lys | Leu | Thr | Asp | Ala | Val | Arg | Arg |      |
|     |     | 555 |     |     |     |     | 560 |     |     |     |     | 565 |     |     |     |      |
| TGG | GAT | GCG | GAA | GGG | TTA | GGC | AGC | CAC | AGC | AAG | ACA | ATA | TTT | GAA | GCC | 1779 |
| Trp | Asp | Ala | Glu | Gly | Leu | Gly | Ser | His | Ser | Lys | Thr | Ile | Phe | Glu | Ala |      |
|     | 570 |     |     |     |     | 575 |     |     |     |     | 580 |     |     |     |     |      |
| CTG | GAT | GAT | CTT | GTA | AAT | GAA | GTT | AGA | CTC | AAG | TGT | TTC | CAA | CAA | AAT | 1827 |
| Leu | Asp | Asp | Leu | Val | Asn | Glu | Val | Arg | Leu | Lys | Cys | Phe | Gln | Gln | Asn |      |
| 585 |     |     |     |     | 590 |     |     |     |     | 595 |     |     |     |     | 600 |      |
| GGA | CAA | GAC | ATC | AAA | AAC | AAT | CTC | CAA | CAA | TTA | TGG | TAT | GAA | ACA | TTC | 1875 |
| Gly | Gln | Asp | Ile | Lys | Asn | Asn | Leu | Gln | Gln | Leu | Trp | Tyr | Glu | Thr | Phe |      |
|     |     |     |     | 605 |     |     |     |     | 610 |     |     |     |     | 615 |     |      |
| CAT | TCA | TGG | CTT | ATG | GAA | GCT | AAG | TGG | GGA | AAG | GGG | TTA | ACA | AGT | AAA | 1923 |
| His | Ser | Trp | Leu | Met | Glu | Ala | Lys | Trp | Gly | Lys | Gly | Leu | Thr | Ser | Lys |      |
|     |     |     | 620 |     |     |     |     | 625 |     |     |     |     | 630 |     |     |      |
| CCA | TCT | GTA | GAT | GTG | TAT | CTT | GGA | AAT | GCA | ATG | ACA | TCC | ATA | GCA | GCT | 1971 |
| Pro | Ser | Val | Asp | Val | Tyr | Leu | Gly | Asn | Ala | Met | Thr | Ser | Ile | Ala | Ala |      |
|     |     | 635 |     |     |     |     | 640 |     |     |     |     | 645 |     |     |     |      |
| CAC | ACC | ATG | GTC | CTT | ACA | GCA | TCC | TGT | CTT | CTA | GGT | CCC | GGT | TTC | CCG | 2019 |
| His | Thr | Met | Val | Leu | Thr | Ala | Ser | Cys | Leu | Leu | Gly | Pro | Gly | Phe | Pro |      |
|     | 650 |     |     |     |     | 655 |     |     |     |     | 660 |     |     |     |     |      |
| GTT | CAC | CAA | CTA | TGG | TCG | CAA | AGG | CGC | CAC | CAG | GAC | ATT | ACA | TCC | TTG | 2067 |
| Val | His | Gln | Leu | Trp | Ser | Gln | Arg | Arg | His | Gln | Asp | Ile | Thr | Ser | Leu |      |
| 665 |     |     |     |     | 670 |     |     |     |     | 675 |     |     |     |     | 680 |      |
| CTC | ATG | GTC | TTG | ACT | CGC | TTG | CTA | AAT | GAC | ATT | CAA | TCC | TAC | TTG | AAA | 2115 |
| Leu | Met | Val | Leu | Thr | Arg | Leu | Leu | Asn | Asp | Ile | Gln | Ser | Tyr | Leu | Lys |      |
|     |     |     |     | 685 |     |     |     |     | 690 |     |     |     |     | 695 |     |      |
| GAA | GAA | GAC | GAA | GGA | AAA | ATA | AAC | TAT | GTA | TGG | ATG | TAC | ATG | ATC | GAG | 2163 |
| Glu | Glu | Asp | Glu | Gly | Lys | Ile | Asn | Tyr | Val | Trp | Met | Tyr | Met | Ile | Glu |      |
|     |     |     | 700 |     |     |     |     | 705 |     |     |     |     | 710 |     |     |      |
| AAC | AAT | CAA | GCG | TCG | ATA | GAT | GAC | TCG | GTT | CGA | CAC | GTC | CAG | ACG | ATA | 2211 |
| Asn | Asn | Gln | Ala | Ser | Ile | Asp | Asp | Ser | Val | Arg | His | Val | Gln | Thr | Ile |      |
|     |     | 715 |     |     |     |     | 720 |     |     |     |     | 725 |     |     |     |      |
| ATC | AAT | GTA | AAA | AAG | CAA | GAA | TTC | ATC | CAA | CGT | GTT | CTA | TCG | GAT | CAA | 2259 |
| Ile | Asn | Val | Lys | Lys | Gln | Glu | Phe | Ile | Gln | Arg | Val | Leu | Ser | Asp | Gln |      |
|     | 730 |     |     |     |     | 735 |     |     |     |     | 740 |     |     |     |     |      |
| CAT | TGC | AAT | CTC | CCA | AAG | TCA | TTC | AAG | CAG | CTC | CAT | TTC | TCC | TGC | CTC | 2307 |
| His | Cys | Asn | Leu | Pro | Lys | Ser | Phe | Lys | Gln | Leu | His | Phe | Ser | Cys | Leu |      |
| 745 |     |     |     |     | 750 |     |     |     |     | 755 |     |     |     |     | 760 |      |
| AAA | GTA | TTC | AAC | ATG | TTC | TTC | AAC | TCC | TCC | AAC | ATT | TTC | GAC | ACT | GAT | 2355 |
| Lys | Val | Phe | Asn | Met | Phe | Phe | Asn | Ser | Ser | Asn | Ile | Phe | Asp | Thr | Asp |      |
|     |     |     |     | 765 |     |     |     |     | 770 |     |     |     |     | 775 |     |      |
| ACC | GAC | CTT | CTT | CTT | GAC | ATT | CAC | GAA | GCT | TTT | GTT | TCT | CCA | CCA | CAA | 2403 |
| Thr | Asp | Leu | Leu | Leu | Asp | Ile | His | Glu | Ala | Phe | Val | Ser | Pro | Pro | Gln |      |
|     |     |     | 780 |     |     |     |     | 785 |     |     |     |     | 790 |     |     |      |
| GTT | CCC | AAA | TTC | AAA | CCC | CAC | ATC | AAG | CCA | CCT | CAT | CAG | CTT | CCA | GCA | 2451 |
| Val | Pro | Lys | Phe | Lys | Pro | His | Ile | Lys | Pro | Pro | His | Gln | Leu | Pro | Ala |      |
|     |     | 795 |     |     |     |     | 800 |     |     |     |     | 805 |     |     |     |      |
| ACA | CTT | CAG | CCA | CCT | CAT | CAG | CCC | CAA | CAA | ATA | ATG | GTC | AAT | AAG | AAG | 2499 |
| Thr | Leu | Gln | Pro | Pro | His | Gln | Pro | Gln | Gln | Ile | Met | Val | Asn | Lys | Lys |      |
|     | 810 |     |     |     |     | 815 |     |     |     |     | 820 |     |     |     |     |      |
| AAG | GTG | GAA | ATG | GTT | TAC | AAA | AGC | TAT | CAT | CAT | CCA | TTC | AAG | GTT | TTC | 2547 |
| Lys | Val | Glu | Met | Val | Tyr | Lys | Ser | Tyr | His | His | Pro | Phe | Lys | Val | Phe |      |
| 825 |     |     |     |     | 830 |     |     |     |     | 835 |     |     |     |     | 840 |      |
| ACC | TTG | CAG | AAG | AAA | CAA | AGT | TCG | GGA | CAT | GGT | ACA | ATG | AAT | CCA | AGG | 2595 |
| Thr | Leu | Gln | Lys | Lys | Gln | Ser | Ser | Gly | His | Gly | Thr | Met | Asn | Pro | Arg |      |
|     |     |     |     | 845 |     |     |     |     | 850 |     |     |     |     | 855 |     |      |
| GCT | AGT | ATC | TTA | GCA | GGA | CCC | AAC | ATC | AAA | CTA | TGT | TTC | AGT |     |     | 2637 |
| Ala | Ser | Ile | Leu | Ala | Gly | Pro | Asn | Ile | Lys | Leu | Cys | Phe | Ser |     |     |      |

```
                        860                    865                    870
TAACGAATAC   ACTACCTTGT   TATTAGAAGA   TGTCACCAGT   TTCC                                          2681
```

( 2 ) INFORMATION FOR SEQ ID NO:2:

( i ) SEQUENCE CHARACTERISTICS:
        ( A ) LENGTH: 870 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Gln  Leu  Ile  Thr  Asn  Phe  Ser  Ser  Ser  Ser  Ser  Glu  Leu  Gln  Phe
  1                  5                       10                      15

Leu  Val  Asp  Lys  Val  Lys  Arg  Glu  Ser  Leu  Ser  Ser  Ser  Ser  Ser  Asn
               20                       25                      30

Thr  Gln  Asn  Leu  Phe  Leu  Ser  Thr  Ser  Pro  Tyr  Asp  Thr  Ala  Trp  Leu
          35                       40                      45

Ala  Leu  Ile  Pro  His  Pro  His  His  His  His  His  Gly  Arg  Pro  Met
     50                  55                      60

Phe  Glu  Lys  Cys  Leu  Gln  Trp  Ile  Leu  His  Asn  Gln  Thr  Pro  Gln  Gly
 65                       70                      75                      80

Phe  Trp  Ala  Ala  Ala  Gly  Asp  Asn  Ile  Ser  Asp  Thr  Asp  Asp  Asp  Val
                    85                      90                      95

Thr  Leu  Asp  Cys  Leu  Leu  Ser  Thr  Leu  Ala  Cys  Leu  Val  Ala  Leu  Lys
                    100                     105                     110

Arg  Trp  Gln  Leu  Ala  Pro  Asp  Met  Ile  His  Lys  Gly  Leu  Glu  Phe  Val
               115                      120                     125

Asn  Arg  Asn  Thr  Glu  Arg  Leu  Val  Met  Lys  Gln  Lys  Pro  Ser  Asp  Val
          130                      135                     140

Pro  Arg  Trp  Phe  Thr  Ile  Met  Phe  Pro  Ala  Met  Leu  Glu  Leu  Ala  Gly
145                      150                     155                     160

Ala  Ser  Ser  Leu  Arg  Val  Asp  Phe  Ser  Glu  Asn  Leu  Asn  Arg  Ile  Leu
                    165                     170                     175

Val  Glu  Leu  Ser  Gln  Asn  Arg  Asp  Asp  Ile  Leu  Thr  Arg  Glu  Glu  Val
               180                      185                     190

Asp  Glu  Lys  Lys  Gln  Tyr  Ser  Pro  Leu  Leu  Leu  Phe  Leu  Glu  Ala  Leu
          195                      200                     205

Pro  Ala  Gln  Ser  Tyr  Asp  Asn  Asp  Val  Leu  Lys  Gln  Ile  Ile  Asp  Lys
210                      215                     220

Asn  Leu  Ser  Asn  Asp  Gly  Ser  Leu  Leu  Gln  Ser  Pro  Ser  Ala  Thr  Ala
225                      230                     235                     240

Arg  Ala  Tyr  Met  Ile  Thr  Gly  Asn  Thr  Arg  Cys  Leu  Ser  Tyr  Leu  His
                    245                     250                     255

Ser  Leu  Thr  Asn  Ser  Cys  Ser  Asn  Gly  Gly  Val  Pro  Ser  Phe  Tyr  Pro
               260                      265                     270

Val  Asp  Asp  Asp  Leu  His  Asp  Leu  Val  Met  Val  Asn  Gln  Leu  Thr  Arg
          275                      280                     285

Ser  Gly  Leu  Thr  Glu  His  Leu  Ile  Pro  Glu  Ile  Asp  His  Leu  Leu  Leu
     290                      295                     300

Lys  Val  Gln  Lys  Asn  Tyr  Lys  Tyr  Lys  Lys  His  Gln  Asn  His  Cys
305                      310                     315                     320

Ile  Ala  Leu  Leu  Arg  Asn  Tyr  Thr  Gly  Phe  Ile  Ser  Ile  Phe  Gly  Cys
                    325                     330                     335

Phe  Glu  Ser  Ile  Ile  Thr  Gly  Tyr  His  His  Gln  Phe  Phe  Cys  Trp  Phe
```

|   |   |   |   |   | 340 |   |   |   |   | 345 |   |   |   |   | 350 |   |   |
|---|---|---|---|---|---|---|---|---|---|---|---|---|---|---|---|---|---|

Leu Asp Asp Asp Glu Ile Arg Asp His Ile Glu Thr Asn Tyr Glu Glu
            355             360                 365

Phe Ala Ala Val Leu Leu Asn Val Tyr Arg Ala Thr Asp Leu Met Phe
    370             375             380

Ser Gly Glu Val Gln Leu Val Glu Ala Arg Ser Phe Ala Thr Lys Asn
385             390             395                         400

Leu Glu Lys Ile Leu Ala Thr Gly Asn Ile His Lys Thr Asn Ala Asp
                405             410                     415

Ile Ser Ser Ser Leu His Lys Met Ile Glu His Glu Leu Arg Val Pro
            420             425                     430

Trp Thr Ala Arg Met Asp His Val Glu Asn Arg Ile Trp Ile Glu Glu
            435             440             445

Ile Ala Ser Ser Ala Leu Trp Phe Gly Lys Ser Ser Ile Leu Arg Leu
    450             455                     460

Ser Cys Phe His Lys Met Ser Leu Gln Gln Leu Ala Val Lys Asn Tyr
465             470             475                         480

Thr Leu Arg Gln Leu Val Tyr Arg Asp Glu Leu Ala Glu Val Glu Arg
                485             490                     495

Trp Ser Lys Glu Arg Gly Leu Cys Asp Met Gly Phe Cys Arg Glu Lys
            500             505             510

Thr Gly Tyr Cys Tyr Tyr Ala Phe Ala Ala Ser Thr Cys Leu Pro Trp
            515             520             525

Ser Ser Asp Val Arg Leu Val Leu Thr Lys Ala Ala Val Val Ile Thr
            530             535             540

Val Ala Asp Asp Phe Phe Asp Val Glu Gly Ser Met Val Asp Leu Glu
545             550             555                         560

Lys Leu Thr Asp Ala Val Arg Arg Trp Asp Ala Glu Gly Leu Gly Ser
            565             570             575

His Ser Lys Thr Ile Phe Glu Ala Leu Asp Asp Leu Val Asn Glu Val
            580             585             590

Arg Leu Lys Cys Phe Gln Gln Asn Gly Gln Asp Ile Lys Asn Asn Leu
        595             600             605

Gln Gln Leu Trp Tyr Glu Thr Phe His Ser Trp Leu Met Glu Ala Lys
610                 615             620

Trp Gly Lys Gly Leu Thr Ser Lys Pro Ser Val Asp Val Tyr Leu Gly
625             630             635                         640

Asn Ala Met Thr Ser Ile Ala Ala His Met Val Leu Thr Ala Ser
                645             650                     655

Cys Leu Leu Gly Pro Gly Phe Pro Val His Gln Leu Trp Ser Gln Arg
            660             665             670

Arg His Gln Asp Ile Thr Ser Leu Leu Met Val Leu Thr Arg Leu Leu
        675             680             685

Asn Asp Ile Gln Ser Tyr Leu Lys Glu Glu Asp Glu Gly Lys Ile Asn
690                     695             700

Tyr Val Trp Met Tyr Met Ile Glu Asn Asn Gln Ala Ser Ile Asp Asp
705             710             715                         720

Ser Val Arg His Val Gln Thr Ile Ile Asn Val Lys Lys Gln Glu Phe
            725             730             735

Ile Gln Arg Val Leu Ser Asp Gln His Cys Asn Leu Pro Lys Ser Phe
            740             745             750

Lys Gln Leu His Phe Ser Cys Leu Lys Val Phe Asn Met Phe Phe Asn
        755             760             765

-continued

| | | | | | | | | | | | | | | |
|---|---|---|---|---|---|---|---|---|---|---|---|---|---|---|
| Ser | Ser 770 | Asn | Ile | Phe | Asp | Thr 775 | Asp | Thr | Asp | Leu | Leu 780 | Leu | Asp | Ile | His |
| Glu 785 | Ala | Phe | Val | Ser | Pro 790 | Pro | Gln | Val | Pro | Lys 795 | Phe | Lys | Pro | His | Ile 800 |
| Lys | Pro | Pro | His | Gln 805 | Leu | Pro | Ala | Thr | Leu 810 | Gln | Pro | Pro | His | Gln 815 | Pro |
| Gln | Gln | Ile | Met 820 | Val | Asn | Lys | Lys | Lys 825 | Val | Glu | Met | Val | Tyr 830 | Lys | Ser |
| Tyr | His | His 835 | Pro | Phe | Lys | Val | Phe 840 | Thr | Leu | Gln | Lys | Lys 845 | Gln | Ser | Ser |
| Gly | His 850 | Gly | Thr | Met | Asn | Pro 855 | Arg | Ala | Ser | Ile | Leu 860 | Ala | Gly | Pro | Asn |
| Ile 865 | Lys | Leu | Cys | Phe | Ser 870 | | | | | | | | | | |